(12) United States Patent
Hofmeister et al.

(10) Patent No.: US 7,858,619 B2
(45) Date of Patent: Dec. 28, 2010

(54) SUBSTITUTED TETRAHYDROISOCHINOLINES AS MMP INHIBITORS, RELATED PRODUCTION METHOD AND USE AS MEDICINE

(75) Inventors: Armin Hofmeister, Frankurt am Main (DE); Manfred Schudok, Eppstein/Ts (DE); Hans Matter, Langenselbold (DE); Kristin Breitschopf, Offenbach (DE); Antonio Ugolini, Paris (FR)

(73) Assignee: sanofi-aventis, Paris (FR)

( * ) Notice: Subject to any disclaimer, the term of this patent is extended or adjusted under 35 U.S.C. 154(b) by 631 days.

(21) Appl. No.: 11/862,818

(22) Filed: Sep. 27, 2007

(65) Prior Publication Data

US 2008/0090821 A1 Apr. 17, 2008

Related U.S. Application Data

(63) Continuation of application No. PCT/EP2006/002440, filed on Mar. 17, 2006.

(30) Foreign Application Priority Data

Mar. 31, 2005 (DE) ........................ 10 2005 015 040

(51) Int. Cl.
*C07D 401/02* (2006.01)
*A61K 31/47* (2006.01)
(52) U.S. Cl. .............................. 514/235.2; 514/253.05; 514/309; 544/128; 544/363; 546/141
(58) Field of Classification Search ........................ None
See application file for complete search history.

(56) References Cited

U.S. PATENT DOCUMENTS 5,962,471 A 10/1999 Schudok et al.

FOREIGN PATENT DOCUMENTS

| DE | 102004031850 | 1/2006 |
|----|--------------|--------|
| WO | WO 97/18194 | 5/1997 |
| WO | WO 03/016248 | 2/2003 |

OTHER PUBLICATIONS

Ma, Dawei, et al., Tetrahydroisoquinoline based sulfonamide hydroxamates as potent matrix metalloproteinase inhibitors, Bioorganic and Medicinal Chemistry Letters 14 47-50, Jan. 2004.

*Primary Examiner*—Zinna N Davis
(74) *Attorney, Agent, or Firm*—James W. Bolcsak

(57) ABSTRACT

The present invention is directed to a compound of formula (I),

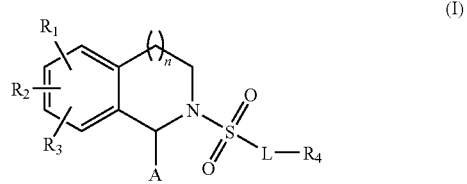

wherein $R_1$, $R_2$, $R_3$, $R_4$, A, L and n are as defined herein, its pharmaceutical composition, preparation and uses as a MMP inhibitor.

15 Claims, No Drawings

SUBSTITUTED TETRAHYDROISOCHINOLINES AS MMP INHIBITORS, RELATED PRODUCTION METHOD AND USE AS MEDICINE

This application is a Continuation of International Application No. PCT/EP2006/002440, filed Mar. 17, 2006.

BACKGROUND OF THE INVENTION

In diseases such as osteoarthritis and rheumatism there is destruction of the joint caused in particular by the proteolytic breakdown of collagen by collagenases. Collagenases belong to the superfamily of metalloproteinases (MP) or matrix metalloproteinases (MMP or MMPs). The MMPs form a group of Zn-dependent enzymes involved in the biodegradation of the extracellular matrix (D. Yip et al., Investigational New Drugs 1999, 17, 387-399 and Michaelides et al., Current Pharmaceutical Design 1999, 5, 787-819). These MMPs are capable in particular of breaking down fibrillary and non-fibrillary collagen, and proteoglycans, both of which represent important matrix constituents. MMPs are involved in processes of wound healing, of tumor invasion, metastasis migration and in angiogenesis, multiple sclerosis and heart failure (Michaelides et al., ibid, page 788). In particular they play an important part in the breakdown of the joint matrix in arthrosis and arthritis, whether osteoarthrosis, osteoarthritis or rheumatoid arthritis.

The activity of MMPs is moreover essential for many of the processes involved in atherosclerotic plaque formation, such as infiltration of inflammatory cells, smooth muscle cell migration, and proliferation and angiogenesis (S. J. George, Exp. Opin. Invest. Drugs 2000, 9 (5), 993-1007). Moreover, matrix degradation by MMP may cause plaque instabilities or even ruptures, possibly leading to the signs and symptoms of atherosclerosis, unstable angina pectoris, myocardial infarction or stroke (E. J. M. Creemers et al, Circulation Res. 2001, 89, 201-210). Considered overall, the entire MMP family can break down all the components of the extracellular matrix of the blood vessels; their activity is therefore subject in a high degree to regulatory mechanisms in normal blood vessels. Elevated MMP activity during plaque formation and plaque instability is caused by increased cytokine- and growth factor-stimulated gene transcription, increased zymogen activation and an imbalance in the MMP-TIMP ratio (tissue inhibitors of metalloproteases). MMP inhibition or restoration of the MMP-TIMP balance is therefore of assistance in the treatment of atherosclerotic disorders. In addition, besides atherosclerosis, other cardiovascular disorders are also at least partly caused by an elevated MMP activity, such as, for example, restenosis, dilated cardiomyopathy and the myocardial infarction which has already been mentioned. It has been possible to show in experimental animal models of these disorders that distinct improvements are achieved by administration of synthetic MMP inhibitors, e.g. relating to the formation of atherosclerotic lesions, neointima formation, left ventricular remodeling, dysfunction of pumping efficiency or healing of infarctions. Detailed tissue analysis in various preclinical studies with MMP inhibitors showed reduced collagen damage, improved extracellular matrix remodeling and an improved structure and function of myocardium and vessels. Of these processes, in particular matrix remodeling processes and MMP-regulated fibroses are regarded as important components in the progression of heart diseases (infarction) (Drugs 2001, 61, 1239-1252).

MMPs cleave matrix proteins such as collagen, laminin, proteoglycans, elastin or gelatin, and MMPs moreover process (i.e. activate or deactivate) by cleavage a large number of other proteins and enzymes under physiological conditions, so that they are important in the whole body, with particular importance in connective tissue and bone.

Substituted tetrahydroisoquinolines were described as inhibitors of MMPs for example in the patent applications WO9718194, CN1380288A, WO03016248 and DE102004031850.6, and in Bioorg. Med. Chem. Lett. 2004, 14, 47-50 and Current Medicinal Chemistry 2001, 8, 425-474.

The compounds of the present invention are usually distinguished by an improved solubility and by a lower tendency to bind to plasma proteins and a greater activity, especially in serum-based assay systems. The improved properties were achieved according to the invention through incorporation of at least one solubility-increasing group X-Q-Y which reduces the lipophilicity of the compounds of the invention.

SUMMARY OF THE INVENTION

The present invention therefore relates to a compound of the formula (I)

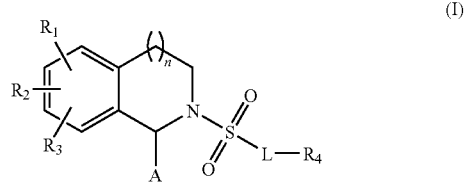

where $R_1$, $R_2$ and $R_3$ are independently of one another H, F, Cl, Br, I, $NO_2$, CN, OH, $(C_1\text{-}C_6)$alkyl, $(C_2\text{-}C_6)$alkenyl, $(C_3\text{-}C_8)$cycloalkyl, $(C_1\text{-}C_4)$alkylene-$(C_3\text{-}C_8)$cycloalkyl, $(C_3\text{-}C_8)$cycloalkylene-$(C_1\text{-}C_4)$alkyl, $O(C_1\text{-}C_6)$alkyl, $O(C_2\text{-}C_6)$alkenyl, $O(C_3\text{-}C_8)$cycloalkyl, $O(C_1\text{-}C_4)$alkylene-$(C_3\text{-}C_8)$cycloalkyl, $O(C_3\text{-}C_8)$cycloalkylene-$(C_1\text{-}C_4)$alkyl, OC(O)—$(C_1\text{-}C_6)$alkyl, OC(O)—$(C_2\text{-}C_6)$alkenyl, OC(O)—$(C_3\text{-}C_8)$cycloalkyl, OC(O)—$(C_1\text{-}C_4)$alkylene-$(C_3\text{-}C_8)$cycloalkyl, OC(O)—$(C_3\text{-}C_8)$cycloalkylene-$(C_1\text{-}C_4)$alkyl, C(O)O—$(C_1\text{-}C_6)$alkyl, C(O)O—$(C_2\text{-}C_6)$alkenylene, C(O)O—$(C_3\text{-}C_8)$cycloalkyl, C(O)O—$(C_1\text{-}C_4)$alkyl-$(C_3\text{-}C_8)$cycloalkyl, C(O)O—$(C_3\text{-}C_8)$cycloalkylene-$(C_1\text{-}C_4)$alkyl, $C(O)NR_5R_6$, $NR_5R_6$, $NR_5C(O)R_6$ or a group X-Q-Y, where X is a covalent bond, O, S, $NR_7$, $C(O)NR_7$, $SO_2$ or $SO_2NR_7$, Q is $(C_1\text{-}C_4)$alkylene, CH=CH or C≡C, Y is $OR_8$, $NR_8R_9$, $C(O)OR_8$, $S(O)_2OR_8$, $SO_2NR_8R_9$, a five- or six-membered saturated heterocycloalkyl radical having 1, 2, 3 or 4 N and/or O atoms, in which the N atoms are substituted by H or $(C_1\text{-}C_6)$alkyl, or Y is a five- or six-membered heteroaryl radical having 1, 2, 3 or 4 N atoms, where 1, 2 or 3, preferably one radical $R_1$, $R_2$ or $R_3$ is described by X-Q-Y, A is $C(O)OR_{10}$, $C(O)NR_{10}R_{11}$, $C(O)NR_{10}OH$ or $CH_2SH$, n is 0, 1 or 2, L is defined by O, NH, $N(C_1\text{-}C_6)$alkyl, a covalent bond or $(C_1\text{-}C_4)$alkylene, $R_4$ is phenyl or $(C_5\text{-}C_{14})$heteroaryl, where the phenyl or $(C_5\text{-}C_{14})$heteroaryl radical is unsubstituted or is substituted by a group T-Z, where T is defined by a covalent bond, O, S, O($C_1$-$C_4$)alkylene, N($R_{12}$), C(O), C(O)O, OC(O), C(O)N($R_{10}$), N($R_{12}$)—C(O) or N($R_{12}$)—C(O)—N($R_{13}$), Z is selected from the group of phenyl, ($C_5$-$C_{14}$)heteroaryl or ($C_3$-$C_8$)heterocycloalkyl, where phenyl, ($C_5$-$C_{14}$)heteroaryl or ($C_3$-$C_8$)heterocycloalkyl in the radical Z is unsubstituted or is substituted by 1, 2 or 3 substituents independently of one another selected from the group of F, Cl, Br, I, CN, OH, $NO_2$, ($C_1$-$C_6$) alkyl, $SO_2$($C_1$-$C_6$)alkyl, O($C_1$-$C_4$)alkylene-O—($C_1$-$C_6$)alkyl, ($C_1$-$C_4$)alkylene-C(O)—O($C_1$-$C_6$)alkyl, O($C_1$-$C_6$)alkyl, ($C_2$-$C_6$)alkenyl, ($C_3$-$C_8$)cycloalkyl, ($C_1$-$C_4$)alkylene-($C_3$-$C_8$)cycloalkyl, ($C_3$-$C_8$)cycloalkylene-($C_1$-$C_4$)alkyl, O($C_2$-$C_6$)alkenyl, O($C_3$-$C_8$)cycloalkyl, O—($C_1$-$C_4$)alkylene-($C_3$-$C_8$)cycloalkyl, O—($C_3$-$C_8$)cycloalkylene-($C_1$-$C_4$)alkyl, ($C_2$-$C_6$)alkynyl, O($C_2$-$C_6$)alkynyl, or $NR_{14}R_{15}$, where $R_{14}$ and $R_{15}$ are defined independently of one another by H, ($C_1$-$C_6$)alkyl, ($C_2$-$C_6$)alkenyl, ($C_3$-$C_8$) cycloalkyl, ($C_1$-$C_4$)alkylene-($C_3$-$C_8$)cycloalkyl, —($C_3$-$C_8$)cycloalkylene-($C_1$-$C_4$)alkyl, ($C_2$-$C_6$)alkynyl, C(O)—($C_1$-$C_6$)alkyl, C(O)—O—($C_1$-$C_6$)alkyl, C(O)—NH—($C_1$-$C_6$)alkyl, C(O)—($C_2$-$C_6$)alkenyl, C(O)—O—($C_2$-$C_6$)alkenyl, C(O)—NH—($C_2$-$C_6$) alkenyl, C(O)—($C_3$-$C_8$)cycloalkyl, C(O)—O—($C_3$-$C_8$)cycloalkyl, C(O)—NH—($C_3$-$C_8$)cycloalkyl, C(O)—($C_1$-$C_4$)alkylene-($C_3$-$C_8$)cycloalkyl, C(O)—O—($C_1$-$C_4$)alkylene-($C_3$-$C_8$)cycloalkyl, C(O)—NH—($C_1$-$C_4$)alkylene-($C_3$-$C_8$)cycloalkyl, C(O)—($C_3$-$C_8$)cycloalkylene-($C_1$-$C_4$)alkyl, C(O)—O—($C_3$-$C_8$)cycloalkylene-($C_1$-$C_4$)alkyl, C(O)—NH—($C_3$-$C_8$)cycloalkylene-($C_1$-$C_4$)alkyl, C(O)—($C_2$-$C_6$) alkynyl, C(O)—O—($C_2$-$C_6$)alkynyl or are C(O)—NH—($C_2$-$C_6$)alkynyl, or is substituted by 1, 2 or 3 substituents independently of one another selected from the group of F, Cl, Br, I, CN, OH, $NO_2$, ($C_1$-$C_6$)alkyl, ($C_2$-$C_6$)alkenyl, ($C_2$-$C_6$)alkynyl, ($C_3$-$C_8$)cycloalkyl, ($C_1$-$C_4$)alkylene-($C_3$-$C_8$)cycloalkyl, ($C_3$-$C_8$)cycloalkylene-($C_1$-$C_4$)alkyl, O($C_1$-$C_6$) alkyl, O($C_2$-$C_6$)alkenyl, O($C_2$-$C_6$)alkynyl, O($C_3$-$C_8$) cycloalkyl, O—($C_1$-$C_4$)alkylene-($C_3$-$C_8$)cycloalkyl, O—($C_3$-$C_8$)cycloalkylene-($C_1$-$C_4$)alkyl, O—($C_1$-$C_4$) alkylene-O—($C_1$-$C_6$)alkyl or a radical $NR_{16}R_{17}$, where $R_{16}$ and $R_{17}$ are defined independently of one another by H, ($C_1$-$C_6$)alkyl, ($C_2$-$C_6$)alkenyl, ($C_3$-$C_8$)cycloalkyl, ($C_1$-$C_4$)alkylene-($C_3$-$C_8$)cycloalkyl, —($C_3$-$C_8$)cycloalkylene-($C_1$-$C_4$)alkyl, ($C_2$-$C_6$)alkynyl, C(O)—($C_1$-$C_6$)alkyl, C(O)—O—($C_1$-$C_6$)alkyl, C(O)—NH—($C_1$-$C_6$)alkyl, C(O)—($C_2$-$C_6$)alkenyl, C(O)—O—($C_2$-$C_6$)alkenyl, C(O)—NH—($C_2$-$C_6$)alkenyl, C(O)—($C_3$-$C_8$)cycloalkyl, C(O)—O—($C_3$-$C_8$)cycloalkyl, C(O)—NH—($C_3$-$C_8$)cycloalkyl, C(O)—($C_1$-$C_4$)alkylene-($C_3$-$C_8$)cycloalkyl, C(O)—O—($C_1$-$C_4$)alkylene-($C_3$-$C_8$)cycloalkyl, C(O)—NH—($C_1$-$C_4$)alkylene-($C_3$-$C_8$)cycloalkyl, C(O)—($C_3$-$C_8$) cycloalkylene-($C_1$-$C_4$)alkyl, C(O)—O—($C_3$-$C_8$) cycloalkylene-($C_1$-$C_4$)alkyl, C(O)—NH—($C_3$-$C_8$) cycloalkylene-($C_1$-$C_4$)alkyl, C(O)—($C_2$-$C_6$)alkynyl, C(O)—O—($C_2$-$C_6$)alkynyl or C(O)—NH—($C_2$-$C_6$) alkynyl, or $R_{16}$ and $R_{17}$ together with the N atom to which they are bonded form a 5- or 6-membered heterocycloalkyl radical in which additionally 0, 1 or 2 ring atoms are O and/or N, and N atoms are substituted by H or ($C_1$-$C_6$)alkyl, or $R_{16}$ and $R_{17}$ together with the N atom to which they are bonded form a 5- or 6-membered heteroaryl radical in which additionally 0, 1 or 2 ring atoms are O and/or N, $R_5$, $R_6$, $R_7$, $R_8$, $R_9$, $R_{10}$ and $R_{11}$ are independently of one another H or ($C_1$-$C_6$)alkyl, and $R_{12}$ and $R_{13}$ are independently of one another H or ($C_1$-$C_4$) alkyl, where optionally independently of one another one or more H atoms in ($C_1$-$C_6$)alkyl, ($C_1$-$C_6$)alkylene, ($C_1$-$C_4$)alkyl, ($C_1$-$C_4$)alkylene, ($C_2$-$C_6$)alkenyl, ($C_3$-$C_8$)cycloalkyl, ($C_3$-$C_8$)cycloalkylene or ($C_2$-$C_6$)alkynyl radicals may be replaced by F atoms, or the pharmacologically acceptable salts thereof.

DETAILED DESCRIPTION OF THE INVENTION

The invention preferably relates to a compound of the formula (I) as defined above, in which n is equal to 1. The invention further relates to a compound of the formula (I) as defined above, in which L is a covalent bond or a ($C_1$-$C_4$) alkylene group, in particular a covalent bond. The invention particularly preferably relates to a compound of the formula (I) as defined above, in which n is equal to 1 and in which L is a covalent bond or a ($C_1$-$C_4$)alkylene group, in particular a covalent bond.

Further preferred compounds of the formula (I) as defined above, are those in which $R_4$ is phenyl or ($C_5$-$C_{14}$)heteroaryl, preferably phenyl or ($C_5$-$C_{10}$)heteroaryl, where phenyl or ($C_5$-$C_{14}$) or ($C_5$-$C_{10}$)-heteroaryl is substituted by 1, 2 or 3 substituents, and where one of these substituents is a group T-Z.

Further preferred compounds of the formula (I) as defined above, are those in which A is equal to C(O)$OR_{10}$, C(O) $NR_{10}R_{11}$ or C(O)$NR_{10}$OH.

A further aspect of the invention is a compound of the formula (I) in which $R_1$, $R_2$ and $R_3$ are independently of one another H, F, Cl, Br, CN, OH, ($C_1$-$C_6$)alkyl, ($C_3$-$C_8$)cycloalkyl, O($C_1$-$C_6$)alkyl, O($C_3$-$C_8$)cycloalkyl, OC(O)—($C_1$-$C_6$)alkyl, OC(O)—($C_3$-$C_8$)cycloalkyl, C(O)O—($C_1$-$C_6$)alkyl, C(O)O—($C_3$-$C_8$)cycloalkyl, C(O)$NR_5R_6$, $NR_5R_6$, $NR_5$C(O)$R_6$ or a group X-Q-Y, where X is a covalent bond, O or $NR_7$, Q is ($C_1$-$C_4$)alkylene, Y is $OR_8$, $NR_8R_9$, C(O)$OR_8$, S(O)$_2OR_8$, S(O)$_2NR_8R_9$, a five- or six-membered saturated heterocycle having 1 or 2 N and/or O atoms, in which the N atoms are substituted by H or ($C_1$-$C_6$)-alkyl, or Y is a five- or six-membered aromatic heterocycle having 1, 2 or 3 N atoms, where 1 or 2 radicals $R_1$, $R_2$ or $R_3$ are described by X-Q-Y, A is C(O)$OR_{10}$, C(O)$NR_{10}R_{11}$ or C(O)$NR_{10}$OH, n is 1, L is defined by a covalent bond or ($C_1$-$C_4$)alkylene, $R_4$ is phenyl or ($C_5$-$C_{14}$)heteroaryl, where the phenyl or ($C_5$-$C_{14}$)heteroaryl radical is unsubstituted or is substituted by a group T-Z, where T is defined by a covalent bond, O, NH or N($C_1$-$C_4$)alkyl, Z is selected from the group of phenyl, ($C_5$-$C_{14}$)heteroaryl or ($C_3$-$C_8$)heterocycloalkyl, where phenyl, ($C_5$-$C_{14}$)heteroaryl or ($C_3$-$C_8$)heterocycloalkyl is unsubstituted or is substituted by 1, 2 or 3 substituents independently of one another selected from the group of F, Cl, Br, CN, OH, ($C_1$-$C_6$)alkyl, $SO_2$($C_1$-$C_6$)alkyl, O—($C_1$-$C_4$)alkylene-O—($C_1$-$C_6$)alkyl, O—($C_1$-$C_6$)alkyl, ($C_3$-$C_8$)cycloalkyl, O($C_3$-$C_8$)cycloalkyl, ($C_2$-$C_6$)alkynyl, O($C_2$-$C_6$)alkynyl, or $NR_{14}R_{15}$, where $R_{14}$ and $R_{15}$ are defined independently of one another by H, $(C_1-C_6)$alkyl, $(C_3-C_8)$cycloalkyl, $(C_2-C_6)$alkynyl, C(O)—$(C_1-C_6)$alkyl, C(O)—O—$(C_1-C_6)$alkyl, C(O)—NH—$(C_1-C_6)$alkyl, C(O)—$(C_3-C_8)$cycloalkyl, C(O)—O—$(C_3-C_8)$cycloalkyl, C(O)—NH—$(C_3-C_8)$cycloalkyl, C(O)—$(C_2-C_6)$alkynyl, C(O)—O—$(C_2-C_6)$alkynyl or C(O)—NH—$(C_2-C_6)$alkynyl, or is substituted by 1, 2 or 3 substituents independently of one another selected from the group of F, Cl, Br, CN, OH, $(C_1-C_6)$alkyl, $(C_2-C_6)$alkynyl, $(C_3-C_8)$cycloalkyl, O$(C_1-C_6)$alkyl, O$(C_2-C_6)$alkynyl, O$(C_3-C_8)$cycloalkyl, O—$(C_1-C_4)$alkylene-O—$(C_1-C_6)$alkyl or a radical N$R_{16}R_{17}$, where $R_{16}$ and $R_{17}$ are defined independently of one another by H, $(C_1-C_6)$alkyl, $(C_3-C_8)$cycloalkyl, $(C_2-C_6)$alkynyl, C(O)—$(C_1-C_6)$alkyl, C(O)—O—$(C_1-C_6)$alkyl, C(O)—NH—$(C_1-C_6)$alkyl, C(O)—$(C_3-C_8)$cycloalkyl, C(O)—O—$(C_3-C_8)$cycloalkyl, C(O)—NH—$(C_3-C_8)$cycloalkyl, C(O)—$(C_2-C_6)$alkynyl, C(O)—O—$(C_2-C_6)$alkynyl or C(O)—NH—$(C_2-C_6)$alkynyl, or $R_{16}$ and $R_{17}$ together with the N atom to which they are bonded form a 5- or 6-membered heterocycloalkyl radical in which additionally 0, 1 or 2 ring atoms are O and/or N, and N atoms are substituted by H or $(C_1-C_6)$alkyl, or $R_{16}$ and $R_{17}$ together with the N atom to which they are bonded form a 5- or 6-membered heteroaryl radical in which additionally 0, 1 or 2 ring atoms are O and/or N, $R_5$, $R_6$, $R_7$, $R_8$, $R_9$, $R_{10}$, and $R_{11}$ are independently of one another H or $(C_1-C_6)$alkyl, or the pharmacologically acceptable salts thereof.

A further aspect of the invention is a compound of the formula (I) in which $R_1$, $R_2$ and $R_3$ are independently of one another H, F, Cl, Br, CN, OH, $(C_1-C_6)$alkyl, cyclopropyl, O$(C_1-C_6)$alkyl, acetyl, propionyl, C(O)O—$(C_1-C_4)$alkyl, N$R_5R_6$ or a group X-Q-Y, where X is O, Q is $(C_1-C_4)$alkylene, and Y is O—$(C_1-C_4)$alkyl, N$R_8R_9$, COOH, C(O)O$(C_1-C_4)$alkyl, SO$_3$H, S(O)$_2$O$(C_1-C_4)$alkyl, SO$_2$N$R_8R_9$, a five- or six-membered saturated heterocycle having 1 or 2 N and/or O atoms, in which the N atoms are substituted by H or $(C_1-C_4)$-alkyl, or Y is a five- or six-membered aromatic heterocycle having 1 or 2 N atoms, where one or two radicals $R_1$, $R_2$ or $R_3$ are described by a group X-Q-Y, A is COOH, C(O)NH$_2$ or C(O)NHOH, n is 1, L is a covalent bond, $R_4$ is phenyl or $(C_5-C_{10})$heteroaryl, where the phenyl or $(C_5-C_{10})$heteroaryl radical is unsubstituted or is substituted by a group T-Z, where T is defined by a covalent bond or O, Z is selected from the group of phenyl or $(C_5-C_{10})$heteroaryl, where phenyl or $(C_5-C_{14})$heteroaryl is unsubstituted or is substituted by 1 or 2 substituents independently of one another selected from the group of F, Cl, Br, CN, OH, $(C_1-C_6)$alkyl, O—$(C_1-C_4)$alkylene-O—$(C_1-C_6)$alkyl, O—$(C_1-C_6)$alkyl, $(C_2-C_6)$alkynyl, O$(C_2-C_6)$alkynyl, or is substituted by 1 or 2 substituents independently of one another selected from the group of F, Cl, Br, CN, OH, $(C_1-C_4)$alkyl, $(C_2-C_4)$alkynyl, O$(C_1-C_4)$alkyl, O$(C_2-C_4)$alkynyl, O—$(C_1-C_4)$alkylene-O—$(C_1-C_4)$alkyl or a radical N$R_{16}R_{17}$, where $R_{16}$ and $R_{17}$ are defined independently of one another by H, $(C_1-C_6)$alkyl, C(O)—$(C_1-C_6)$alkyl, C(O)—O—$(C_1-C_6)$alkyl, C(O)—NH—$(C_1-C_6)$alkyl, or $R_{16}$ and $R_{17}$ together with the N atom to which they are bonded form a 5- or 6-membered heterocycloalkyl radical in which additionally 0, 1 or 2 ring atoms are O and/or N, and N atoms are substituted by H or $(C_1-C_6)$alkyl, or $R_{16}$ and $R_{17}$ together with the N atom to which they are bonded form a 5- or 6-membered heteroaryl radical in which additionally 0, 1 or 2 ring atoms are O and/or N, $R_5$ and $R_6$ are independently of one another H or $(C_1-C_6)$alkyl, $R_8$ and $R_9$ are independently of one another H or $(C_1-C_4)$alkyl, or the pharmacologically acceptable salts thereof.

A further preferred aspect of the invention is a compound of the formula (I) in which $R_1$, $R_2$ and $R_3$ are independently of one another H, F, Cl, Br, CN, OH, $(C_1-C_4)$alkyl, O$(C_1-C_6)$alkyl, or a group X-Q-Y, where X is O, Q is $(C_1-C_4)$alkylene, and Y is O—$(C_1-C_4)$alkyl, N$R_8R_9$, COOH, C(O)O$(C_1-C_4)$alkyl, SO$_3$H, S(O)$_2$O$(C_1-C_4)$alkyl or a heterocycle selected from the series piperidinyl, morpholinyl, pyrrolidinyl, imidazolyl, pyrazolyl, piperazinyl or N-methyl-piperazinyl, where one or two radicals $R_1$, $R_2$ or $R_3$ are described by a group X-Q-Y, A is COOH, C(O)NH$_2$ or C(O)NHOH, n is 1, L is a covalent bond, $R_4$ is phenyl, where the phenyl radical is unsubstituted or is substituted by a group T-Z, where T defined by a covalent bond or O, Z is selected from the group of phenyl, where phenyl is unsubstituted or is substituted by 1 or 2 substituents independently of one another selected from the group of F, Cl, Br, CN, OH, $(C_1-C_6)$alkyl, O—$(C_1-C_4)$alkylene-O—$(C_1-C_6)$alkyl, O—$(C_1-C_6)$alkyl, $(C_2-C_6)$alkynyl, O$(C_2-C_6)$alkynyl, or is substituted by 1 or 2 substituents independently of one another selected from the group of F, Cl, Br, CN, OH, $(C_1-C_4)$alkyl, $(C_2-C_4)$alkynyl, O$(C_1-C_4)$alkyl, O$(C_2-C_4)$alkynyl, O—$(C_1-C_4)$alkylene-O—$(C_1-C_4)$alkyl or a radical N$R_{16}R_{17}$, where $R_{16}$ and $R_{17}$ are defined independently of one another by H, $(C_1-C_6)$alkyl, C(O)—$(C_1-C_6)$alkyl, C(O)—O—$(C_1-C_6)$alkyl, C(O)—NH—$(C_1-C_6)$alkyl, or $R_{16}$ and $R_{17}$ together with the N atom to which they are bonded form a 5- or 6-membered heterocycloalkyl radical in which additionally 0, 1 or 2 ring atoms are O and/or N, and N atoms are substituted by H or $(C_1-C_6)$alkyl, or $R_{16}$ and $R_{17}$ together with the N atom to which they are bonded form a 5- or 6-membered heteroaryl radical in which additionally 0, 1 or 2 ring atoms are O and/or N, $R_8$ and $R_9$ are independently of one another H or $(C_1-C_4)$alkyl, or the pharmacologically acceptable salts thereof.

A further preferred aspect of the invention are compounds of the formula (I) in which $R_1$, $R_2$ and $R_3$ are independently of one another H, F, Cl, Br, CN, ($C_1$-$C_4$)alkyl or a group X-Q-Y, where
  X is O,
  Q is ($C_2$-$C_3$)alkylene, and
  Y is O—($C_1$-$C_4$)alkyl, $NR_8R_9$ or a heterocycle selected from the series piperidinyl, morpholinyl, pyrrolidinyl, imidazolyl, pyrazolyl, piperazinyl or N-methylpiperazinyl, where a radical $R_1$, $R_2$ or $R_3$ is described by a group X-Q-Y, A is COOH or C(O)NHOH, n is 1, L is a covalent bond, $R_4$ is phenyl, where the phenyl radical is unsubstituted or is substituted by a group T-Z, where
  T is O, and
  Z is a phenyl group, where the phenyl group is unsubstituted or is substituted by 1 or 2 substituents independently of one another selected from the group of H, F, Cl, CN, OH, ($C_1$-$C_4$)alkyl, O($C_1$-$C_6$)alkyl, preferably F or O($C_1$-$C_6$)alkyl,
  or is substituted by 1 or 2 ($C_1$-$C_4$)alkylene radicals, $R_8$ and $R_9$ are independently of one another H or ($C_1$-$C_4$) alkyl, or the pharmacologically acceptable salts thereof.

If the compounds of the formulae (I) comprise one or more centers of asymmetry, they may have both the S and the R configuration independently of one another. The compounds may be in the form of pure optical isomers, of diastereomers, of racemates or of mixtures in all ratios thereof.

The term ($C_1$-$C_6$)alkyl means hydrocarbon radicals whose carbon chain is straight-chain or branched and comprises 1 to 6 carbon atoms, for example methyl, ethyl, n-propyl, isopropyl, n-butyl, isobutyl, tertiary butyl, pentyl, isopentyl, neopentyl, hexyl, 2,3-dimethylbutyl or neohexyl. ($C_1$-$C_6$)Alkylene radicals are correspondingly for example methylene, ethylene, n-propylene, isopropylene, n-butylene, isobutylene, tertiary butylene, pentylene, isopentylene, neopentylene, hexylene, 2,3-dimethylbutylene or neohexylene. The term ($C_1$-$C_4$)alkyl means hydrocarbon radicals whose carbon chain is straight-chain or branched and comprises 1 to 4 carbon atoms, for example methyl, ethyl, n-propyl, isopropyl, isobutyl, butyl or tertiary butyl. ($C_1$-$C_4$)Alkylene radicals are correspondingly for example methylene, ethylene, n-propylene, isopropylene, n-butylene, isobutylene, tertiary butylene. A ($C_1$-$C_6$)alkyl or alkylene group in which one or more H atoms are replaced by F atoms is for example trifluoromethyl, trifluoroethyl, trifluoromethylene or trifluoroethylene. An O($C_1$-$C_6$)alkyl group for example methoxy, ethoxy. An O($C_1$-$C_6$)alkyl group in which one or more H atoms are replaced by F atoms is for example trifluoromethoxy or trifluoroethoxy.

The term ($C_2$-$C_6$)alkenyl means hydrocarbon radicals whose carbon chain comprises 2 to 6 carbon atoms and, depending on the chain length, is straight-chain or branched and has 1, 2 or 3 double bonds, for example ethenyl, propenyl, isopropenyl, isobutenyl or butenyl.

($C_2$-$C_6$)Alkenylene radicals are correspondingly for example ethenylene, propenylene, isopropenylene, isobutenylene or butenylene. The substituents on the double bond may, where the possibility exists in principle, be arranged in the E or Z configuration. The double bonds may be both internal and terminal.

The term ($C_2$-$C_6$)alkynyl means hydrocarbon radicals whose carbon chain comprises 2 to 6 carbon atoms and, depending on the chain length is straight-chain or branched and have 1-3, preferably 1 or 2 triple bonds, for example ethynyl, n-propynyl, isopropynyl, isobutylynyl, butynyl, pentynyl or isomers of pentynyl or hexynyl or isomers of hexynyl. ($C_2$-$C_6$)Alkynyl radicals are correspondingly for example ethynylene, propenylene, isopropynylene, isobutylynylene, butynylene, pentynylene. The triple bonds may be both internal and terminal.

The term ($C_3$-$C_8$)-cycloalkyl means radicals derived from 3-, 4-, 5-, 6-, 7- or 8-membered monocycles such as cyclopropyl, cyclobutyl, cyclopentyl, cyclohexyl, cycloheptyl or cyclooctyl. A ($C_1$-$C_4$)alkylene-($C_3$-$C_8$)cycloalkyl group is a terminal ($C_3$-$C_8$)cycloalkyl group which is linked via a ($C_1$-$C_4$)alkylene radical, for example cyclopropylmethyl.

The term ($C_3$-$C_8$)-heterocycloalkyl means radicals derived from 3-, 4-, 5-, 6-, 7- or 8-membered monocycles such as cyclopropyl, cyclobutyl, cyclopentyl, cyclohexyl, cycloheptyl or cyclooctyl, in which one or more ring atoms are oxygen atoms, sulfur atoms or nitrogen atoms, e.g. 1, 2, 3 or 4 nitrogen atoms, 1 or 2 oxygen atoms, 1 or 2 sulfur atoms or a combinations of various heteroatoms, for example an oxygen atom and a nitrogen atom. The ($C_3$-$C_8$)-heterocycloalkyl radicals may be attached via all positions, for example via position 1, position 2, position 3, position 4, position 5, position 6, position 7 or position 8. Attachment is possible via a C atom or an N atom. ($C_3$-$C_8$)-Heterocycloalkyl radicals are, for example, pyrrolidinyl, tetrahydrothiophenyl, tetrahydrofuranyl, piperidinyl, pyranyl, dioxanyl, morpholinyl. ($C_5$-$C_6$)-Heterocycloalkyl radicals are preferred, especially ($C_5$-$C_6$)-heterocycloalkyl radicals having 1, 2, 3 or 4 N and/or O atoms, in which N atoms are substituted by H or ($C_1$-$C_6$)alkyl. Morpholinyl is particularly preferred.

($C_5$-$C_{14}$)-Heteroaryl radicals are aromatic mono-, bi- or tricyclic ($C_5$-$C_{14}$) ring compounds in which one or more ring atoms are oxygen atoms, sulfur atoms or nitrogen atoms, e.g. 1, 2, 3 or 4 nitrogen atoms, 1 or 2 oxygen atoms, 1 or 2 sulfur atoms or a combinations of various heteroatoms. ($C_5$-$C_{10}$)-Heteroaryl radicals are aromatic mono-, bi- or tricyclic ($C_5$-$C_{10}$) ring compounds in which one or more ring atoms are oxygen atoms, sulfur atoms or nitrogen atoms, e.g. 1, 2, 3 or 4 nitrogen atoms, 1 or 2 oxygen atoms, 1 or 2 sulfur atoms or a combinations of various heteroatoms. The heteroaryl radicals may be attached via all positions, for example via position 1, position 2, position 3, position 4, position 5, position 6, position 7 or position 8. Examples of ($C_5$-$C_{10}$)— and ($C_5$-$C_{14}$)heteroaryl radicals are 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or -5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. Also included are the corresponding N-oxides of these compounds, for example 1-oxy-2-, 3- or 4-pyridyl.

Particularly preferred heteroaryl radicals are the 5- or 6-membered heteroaryl radicals having 1, 2, 3 or 4 N atoms, for example imidazolyl, pyrazolyl, pyrrolyl, triazolyl, tetrazolyl, thiazolyl and oxazolyl, and pyridyl and pyrimidinyl. Preference is further given to the fused ring systems benzofuranyl, benzimidazolyl and indolyl. Pyrazolyl, indolyl and pyridyl is especially preferred.

Pharmacologically acceptable salts of compounds of the formula (I) mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of physiologically tolerated salts from compounds of the formula (I) which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable for this purpose are both inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic, or trifluoroacetic acid.

The invention further relates to a process for preparing compounds of the formula (I), which is described below.

Side chains of the X-Q-Y type are preferably introduced into positions 5 or 6 of the tetrahydroisoquinoline structure. The process of the invention is explained by way of example below for 5- or 6-substituted compounds of the formula (I) in which X is oxygen and A is COOH or C(O)NHOH:

In the case of the 6-substituted compounds of the formula (VIII) vide infra, ethyl 6-hydroxytetrahydroisoquinolinecarboxylate (II), which can be purchased, is used as starting material and is reacted first with a sulfonyl chloride (III) to result in the corresponding sulfonamides (IV).

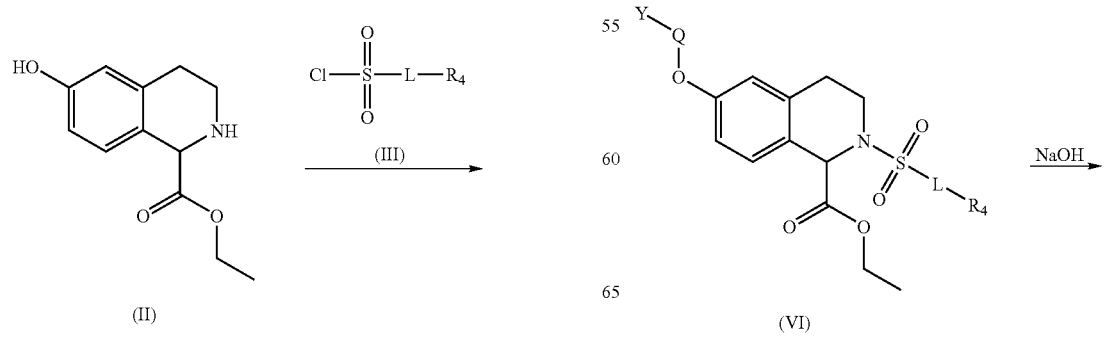

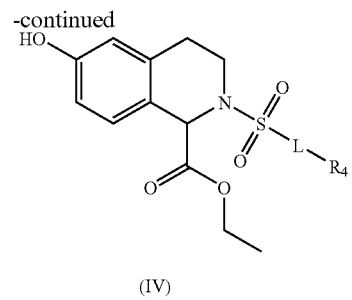

(IV)

The side chain in position 6 is assembled for example by reacting the sulfonamides (IV) with, for example, diethyl azodicarboxylate and triphenylphosphine and the appropriate alcohols (V) to give the desired ethers (VI) having a hydrophilic side chain in position 6. It is possible to employ other dialkyl azodicarboxylates instead of diethyl azodicarboxylate. Also suitable instead of conventional triphenylphosphine are polymer-bound analogs.

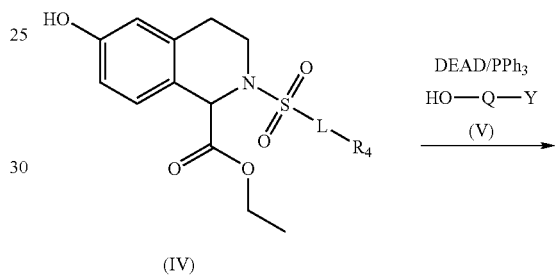

(IV)

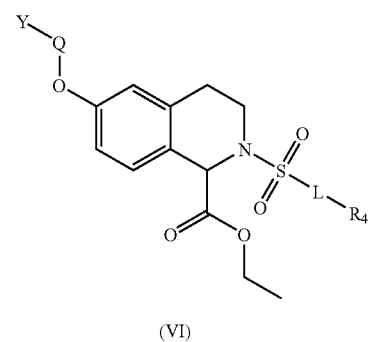

(VI)

Subsequent hydrolysis of the ester function affords the carboxylic acids (VII).

(VI)

-continued

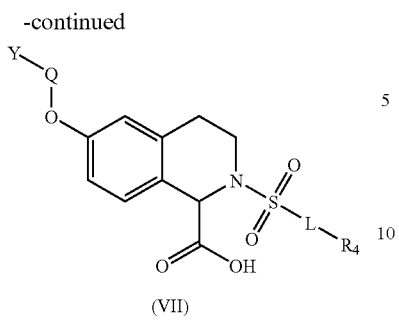

(VII)

These can be converted by methods known to the skilled worker into the analogous hydroxamic acids (VIII).

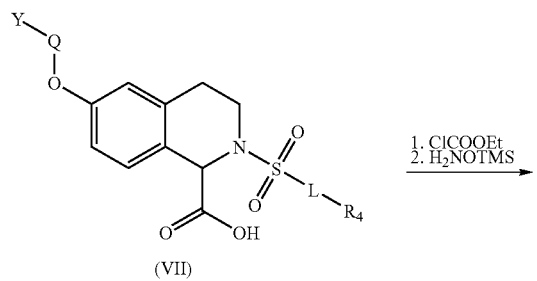

(VII)

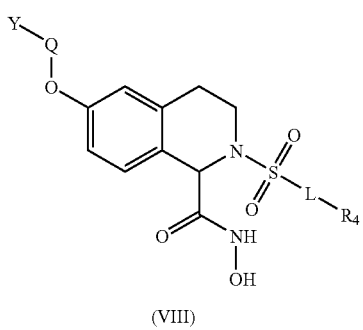

(VIII)

In the case of the analogous 5-substituted compounds of the formula (XVI), commercially available ortho-methoxyphenylethylamine (IX) is used as starting material and is reacted in the first stage initially with a sulfonyl chloride (III) to introduce the desired radical $R_4$, resulting in the sulfonamides (X).

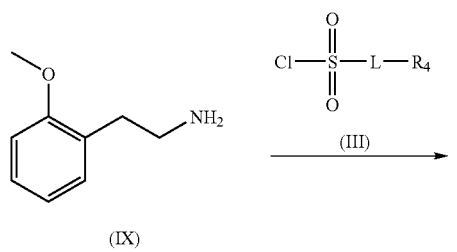

-continued

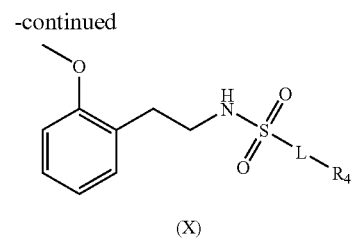

(X)

These can then be converted by a Pictet-Spengler cyclization with glyoxal into the corresponding tetrahydroisoquinoline-1-carboxylic acids (XI).

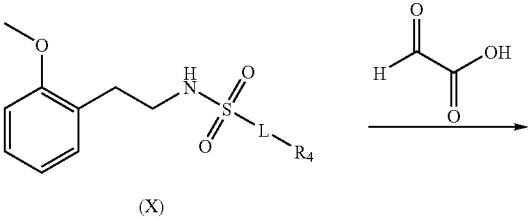

(X)

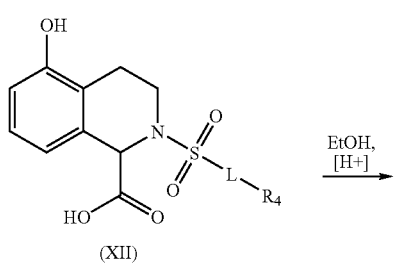

(XI)

Subsequent ether cleavage by boron tribromide affords the free phenol (XII), which can be converted by conventional processes into the analogous ester (XIII).

(XII)

(XIII)

Compound (XIII) is in turn converted in analogy to the Mitsunobu reaction described for (IV) into the corresponding ether (XIV) which now has the hydrophilic side chain in position 5 of the tetrahydroisoquinoline unit.

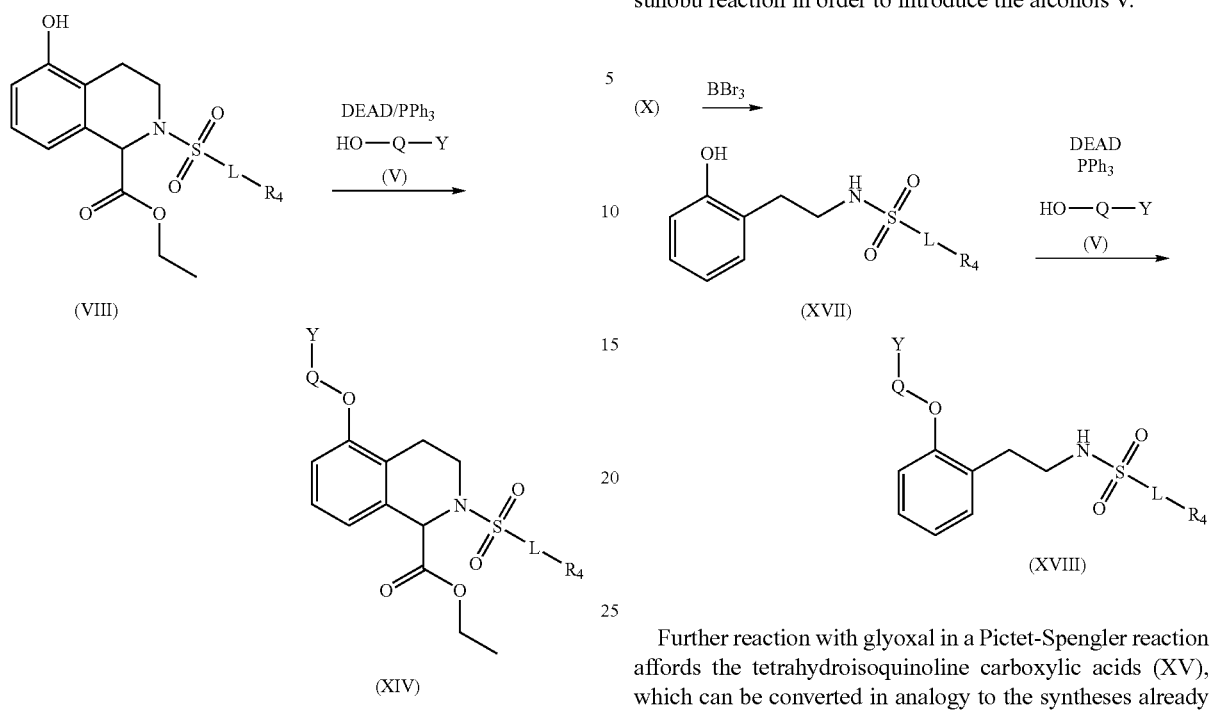

(VIII)
(XIV)

An analogous procedure as for the 6-substituted derivatives affords after hydrolysis the free carboxylic acids (XV) which can then be converted into the analogous hydroxamic acids (XVI).

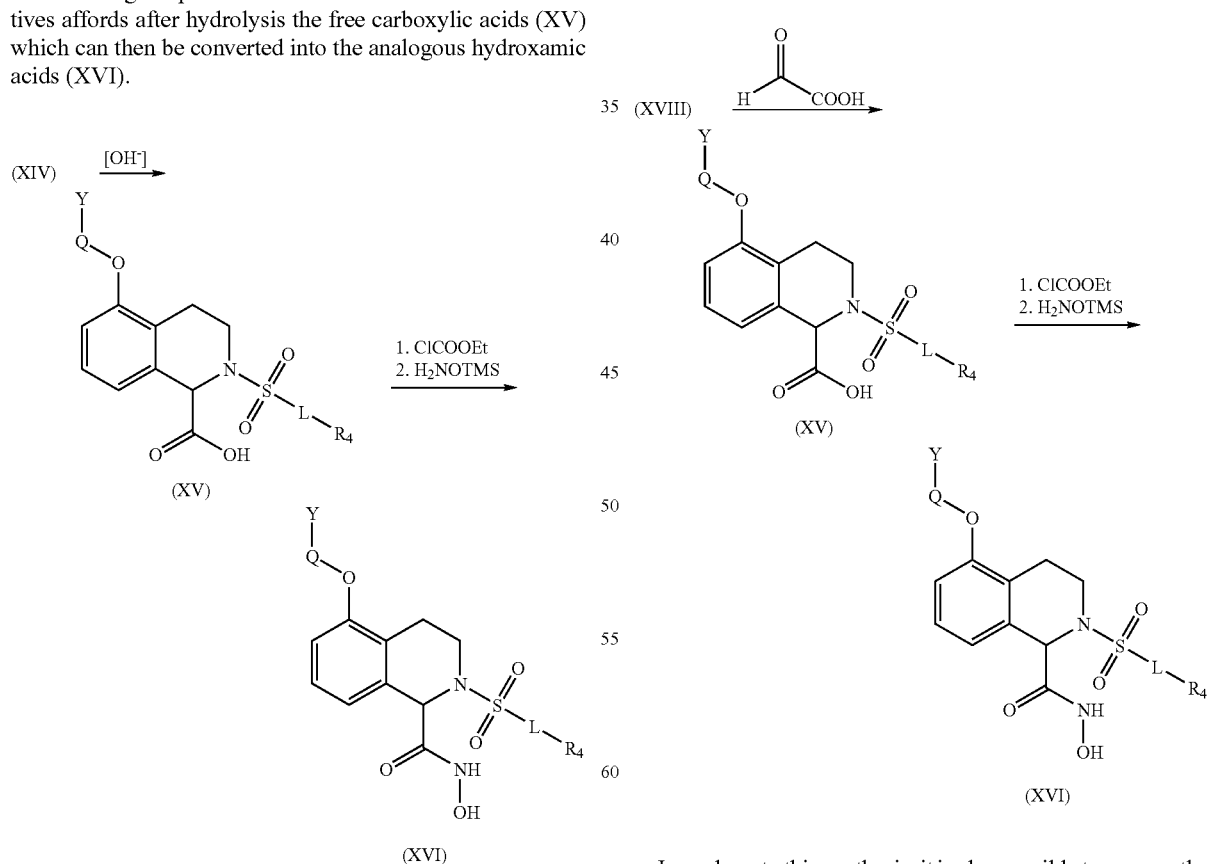

(XV)
(XVI)

As alternative to this, the intermediate compounds X can be cleaved with boron tribromide to give the corresponding phenols (XVII) which can then be employed directly in a Mitsunobu reaction in order to introduce the alcohols V.

Further reaction with glyoxal in a Pictet-Spengler reaction affords the tetrahydroisoquinoline carboxylic acids (XV), which can be converted in analogy to the syntheses already described into the corresponding hydroxamic acids (XVI).

In analogy to this synthesis, it is also possible to prepare the compounds having further substituents on the tetrahydroisoquinoline unit, by using already multiply substituted phenylethylamines (XIX) as starting materials:

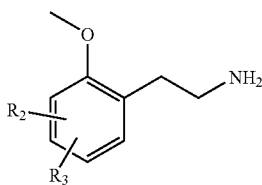
(XIX)

These can be converted in analogy to (IX) by the same synthetic sequences into the desired carboxylic acids (XX) or hydroxamic acids (XXI).

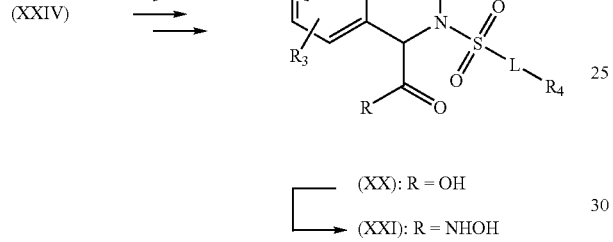

(XXIV) →→

(XX): R = OH
(XXI): R = NHOH

Starting from the syntheses shown for the 5- and 6-substituted tetrahydroisoquinoline-1-carboxylic acids (XX) and (VII) respectively, it is possible to prepare derivatives such as the corresponding esters, thiols or amides as shown in the following general synthesis scheme:

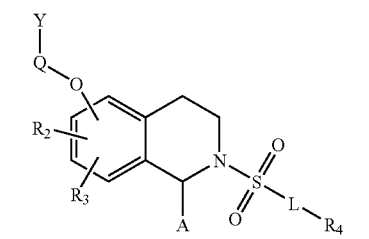

(XX) or (VII) in which in each case A = COOH

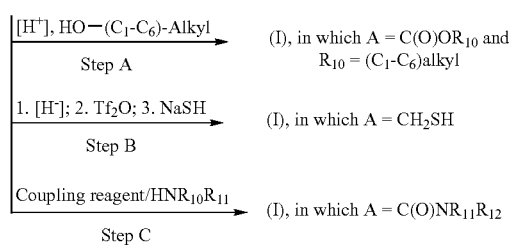

The acid-catalyzed esterification (step A), which is known to the skilled worker, of the carboxylic acids (XX) and (VII) with $(C_1-C_6)$-alkyl alcohols affords compounds of the formula (I) in which A is equal to $C(O)O(C_1-C_6)$alkyl.

Reduction with, for example, $LiAlH_4$, subsequent conversion of the resulting alcohol into a leaving group with, for example, trifluoromethanesulfonic anhydride ($Tf_2O$) and nucleophilic substitution with, for example, NaSH (Step B) affords compounds of the formula (I) in which A is equal to $CH_2SH$.

It is moreover possible for the carboxylic acids (XX) or (VII) also to be converted in the presence of amines $HNR_{10}R_{11}$ by amide-coupling methods known to the skilled worker, such as, for example, mediated by dicyclohexylcarbodiimide, into compounds of the formula (I) in which A is equal to $C(O)NR_{10}R_{11}$.

The invention therefore further relates to a process for preparing a compound of the formula (I), which comprises
in step 1 reacting a tetrahydroisoquinoline of the formula (XXII)

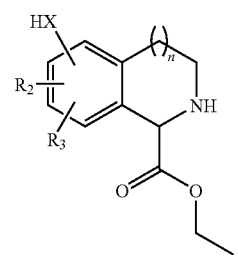
(XXII)

with a sulfonyl chloride (III)

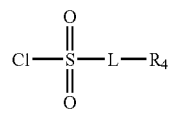
(III)

to form the sulfonamide (XXIII)

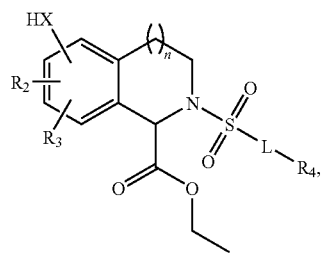
(XXIII)

in step 2 reacting the compound (XXIII) with a dialkyl azodicarboxylate and triphenyl-phosphine and a compound HO-Q-Y (V) to give the compound (XXIV)

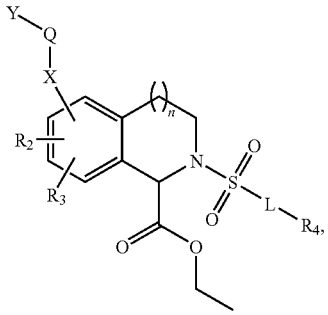
(XXIV)

in step 3 hydrolyzing the ester group in the compound (XXIV) using a base, to form a compound of the formula (I) in which A is C(O)OR$_{10}$, and R$_{10}$ is equal to H, and optionally in step 4 preparing, by acidic esterification through reaction with a (C$_1$-C$_6$)alkyl chloride, a compound of the formula (I) in which A is equal to C(O)OR$_{10}$, and R$_{10}$ is equal to (C$_1$-C$_6$)alkyl, or optionally in step 5 preparing, by reacting with Cl—COOEt and subsequent addition of R$_{10}$HNOTMS, a compound of the formula (I) in which A is equal to C(O)NR$_{10}$OH, or optionally in step 6 preparing a compound of the formula (I) in which A is equal to CH$_2$SH, in which case the carboxylic acid is first reduced with a hydride and, in a following step, the alcohol intermediate produced thereby is provided with a leaving group which affords, by subsequent reaction with a thiolate (SH—), the corresponding thiol, or optionally in step 7 preparing a compound of the formula (I) in which A is equal to C(O)NR$_{10}$R$_{11}$, in which case the carboxylic acid is reacted in the presence of a base with an amine(C$_1$-C$_6$)alkyl-NH$_2$.

It is preferred in the process of the invention for preparing a compound of the formula (I) for n to equal 1.

It has now emerged that the compounds of the invention of the general formula (I) having a side chain of the X-Q-Y type show significantly better solubility in aqueous media than the analogous unsubstituted compounds. Moreover, protein binding is reduced through introduction of the substituent X-Q-Y. It has been possible thereby markedly to improve the activity of the hydroxamic acids in the serum-based assay systems. It has surprisingly also been found that, in the case of compounds of the formula (I) in which A is COOH (carboxylic acids), there is a marked increase in the activity. This is shown in particular in the serum-based assay systems in which carboxylic acid-substituted compounds without the side chains described herein (X-Q-Y) have to date shown no activity.

TABLE 1

Hydroxamic acid derivatives

| No. | Compound of example | Structure | MMP-9* [µM] | Solubility** [µM] | Protein binding (human), [%] | X—Q—Y |
|---|---|---|---|---|---|---|
| 1 | -(Comparative compound) | 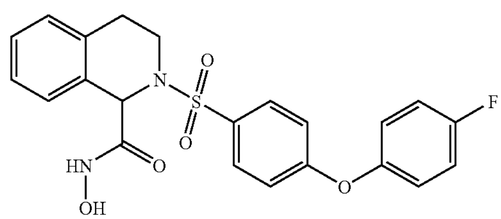 | 2.5 | <1 | 99.8 | Comparative compound without (X—Q—Y) side chain |
| 2 | 3 | 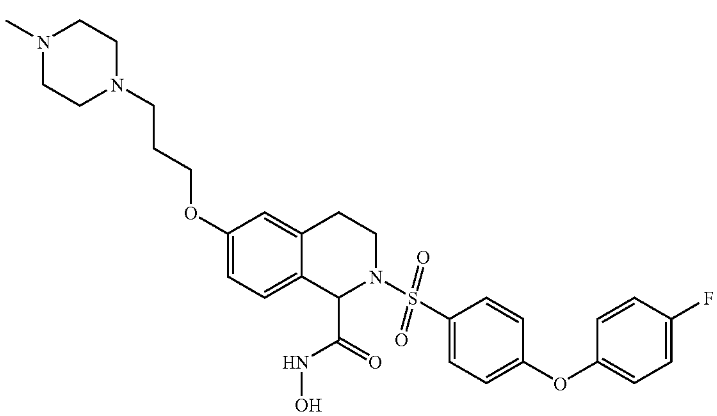 | 0.2 | 23 | 99.0 | 3-(4-Methyl-piperazin-1-yl)propoxy |

TABLE 1-continued

Hydroxamic acid derivatives

| Compound No. | of example | Structure | MMP-9* [μM] | Solubility** [μM] | Protein binding (human), [%] | X—Q—Y |
|---|---|---|---|---|---|---|
| 3 | 9 | 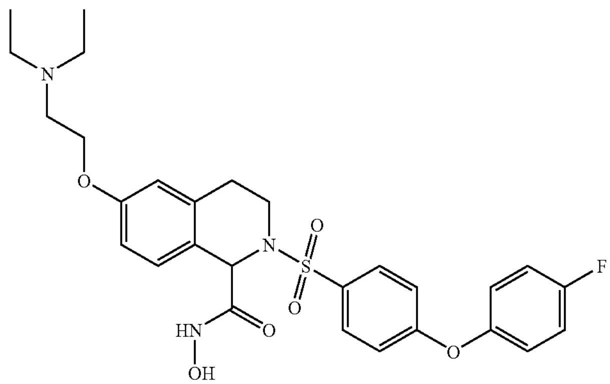 | 0.02 | 153 | 93.9 | 2-Diethylaminoethoxy |
| 5 | 13 | 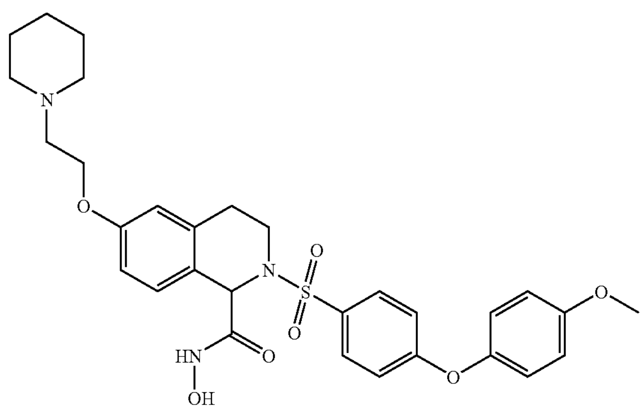 | 0.6 | 16 | 98.9 | 2-Piperidin-1-ylethoxy |
| 4 | 15 | 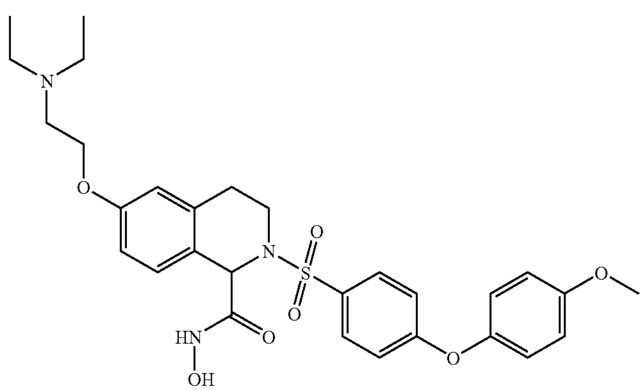 | 0.2 | 107 | 98.8 | 2-Diethylaminoethoxy |

*Serum-based assay;
**Solubility measurements using a CLND (chemoluminescent nitrogen detector)

TABLE 2

Carboxylic acid derivatives

| Compound No. | of example | Structure | MMP-9 activity [µM] | X—Q—Y |
|---|---|---|---|---|
| 1 | -(Comparative compound) | 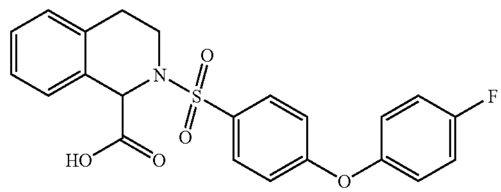 | >100 | Comparative compound without (X—Q—Y) side chain |
| 2 | 2 | 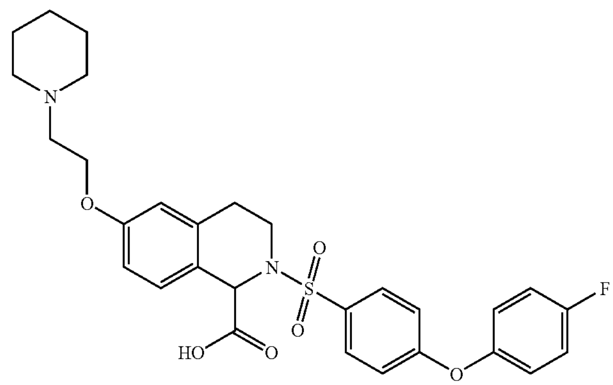 | 8.7 | 2-Piperidin-1-yl-ethoxy |
| 3 | 14 | 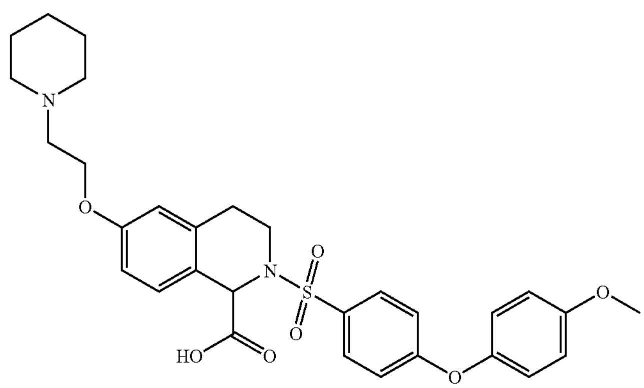 | 7.5 | 2-Piperidin-1-yl-ethoxy |
| 4 | 16 | 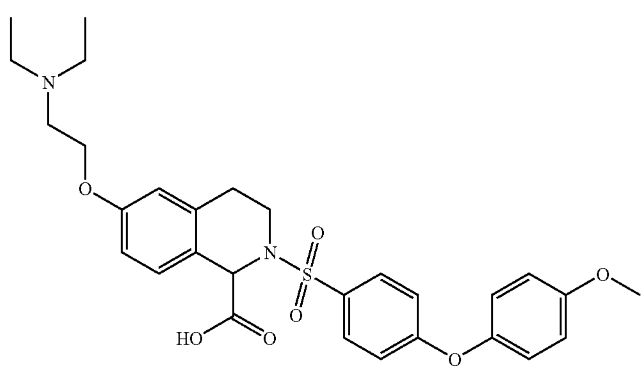 | 6.6 | 2-Diethylamino-ethoxy |

*Serum-based assay

The invention further relates to medicaments comprising a content of at least one compound of the formula (I) and/or of a physiologically tolerated salt of the compound of the formula (I) and/or an optionally stereoisomeric form of the compound of the formula (I), together with a pharmaceutically suitable and physiologically tolerated carrier, additive and/or other active ingredients and excipients.

Because of the pharmacological properties, the compounds of the invention are suitable for the selective prophylaxis and/or therapy of all disorders in the progression of which an enhanced activity of metalloproteinases is involved. These include the indications described in the introduction. The invention relates in particular to the use of a compound of the formula (I) for the treatment of cardiovascular disorders such as remodeling of the heart after a myocardial infarction and atherosclerosis, and of unstable angina pectoris, heart failure, stenosis, septic shock, inflammations, cancers, tumor metastasis, cachexia, anorexia, ulceration, degenerative joint disorders such as osteoarthroses, spondyloses, chondrolysis following joint trauma or prolonged joint immobilization after meniscus or atella injuries or ligament tears, of connective tissue disorders such as collagenoses, periodontal disorders, wound-healing disturbances and chronic disorders of the locomotor system such as inflammatory, immunologically or metabolically related acute and chronic arthritides, arthropathies, myalgias and disturbances of bone metabolism, and the prophylaxis of myocardial and cerebral infarctions.

The medicaments of the invention can be administered by oral, inhalational, rectal or transdermal administration or by subcutaneous, intraarticular, intraperitoneal or intravenous injection. Oral administration is preferred.

The invention also relates to a process for producing a medicament which comprises converting at least one compound of the formula (I) with a pharmaceutically suitable and physiologically tolerated carrier and, where appropriate, further suitable active ingredients, additives or excipients into a suitable dosage form.

Examples of suitable solid or pharmaceutical formulations are granules, powders, coated tablets, tablets, (micro)capsules, suppositories, syrups, oral solutions, suspensions, emulsions, drops or injectable solutions, and products with protracted release of active ingredient, in the production of which conventional physiologically tolerated excipients or carriers such as disintegrants, binders, coating agents, swelling agents, glidants or lubricants, flavorings, sweeteners and solubilizers are used. Excipients which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably produced and administered in dosage units, each unit comprising as active ingredient a particular dose of the compound of the invention of the formula I. In the case of solid dosage units such as tablets, capsules, coated tablets or suppositories, this dose can be up to about 1000 mg, but preferably about 50 to 300 mg, and in the case of solutions for injection in ampoule form up to about 300 mg, but preferably about 10 to 100 mg.

The daily doses indicated for the treatment of an adult patient weighing about 70 kg are from about 2 mg to 1000 mg of active ingredient, preferably about 50 mg to 500 mg, depending on the activity of the compound of the formula (I). However, in some circumstances, higher or lower daily doses may also be appropriate. The daily dose may be administered both by administration once a day in the form of a single dosage unit or else a plurality of smaller dosage units, and by administration more than once a day in divided doses at defined intervals.

The medicaments of the invention are generally administered orally or parenterally, but rectal use is also possible in principle. Examples of suitable solid or liquid pharmaceutical preparations are granules, powders, tablets, coated tablets, (micro)capsules, suppositories, syrups, emulsions, suspensions, aerosols, drops or injectable solutions in ampoule form, and products with protracted release of active ingredient, in the production of which normally carriers and additions and/or aids such as disintegrants, binders, coating agents, swelling agents, glidants or lubricants, flavorings, sweeteners or solubilizers are used.

Examples of conventional pharmacologically suitable carriers or excipients are magnesium carbonate, titanium dioxide, lactose, mannitol and other sugars, talc, milk protein, gelatin, starch, vitamins, cellulose and its derivatives, animal or vegetable oils, polyethylene glycols and solvents such as, for example, sterile water, alcohols, glycerol and polyhydric alcohols.

The dosage units for oral administration may where appropriate be microencapsulated in order to delay delivery or extend it over a longer period, such as, for example, by coating or embedding the active ingredient in particulate form in suitable polymers, waxes or the like.

The pharmaceutical products are preferably produced and administered in dosage units, each unit comprising as active ingredient a particular dose of one or more compounds of the spirobenzofuran lactam derivatives of the invention. In the case of solid dosage units such as tablets, capsules and suppositories, this dose can be up to about 500 mg, but preferably about 0.1 to 200 mg, and in the case of solutions for injection in ampoule form up to about 200 mg, but preferably about 0.5 to 100 mg, per day.

The daily dose to be administered depends on the body weight, age, gender and condition of the mammal. However, in some circumstances higher or lower daily doses may also be appropriate. The daily dose may be administered both by administration once a day in the form of a single dosage unit or else in a plurality of smaller dosage units, and by administration more than once a day in divided doses at defined intervals.

The medicaments of the invention are produced by converting one or more of the compounds of the invention of the formula (I) with one or more of the conventional carriers or excipients into a suitable dosage form.

The invention is explained further in the examples which follow. Percentage data relate to weight. Mixing ratios in the case of liquids relate to volume unless other statements have been made.

EXAMPLES

| List of abbreviations used: | |
|---|---|
| abs. | absolute |
| ACN | Acetonitrile |
| conc. | concentrated |
| comp. | compound |
| DEAD | Diethyl azodicarboxylate |
| DMF | Dimethylformamide |
| eq. | equivalent |

-continued

List of abbreviations used:

| | |
|---|---|
| ESI | electro spray ionization |
| Exp. | Example |
| LCMS | liquid chromatography mass spectrometry |
| Merck | Merck KGaA, Germany |
| $R_t$ | Retention time |
| TFA | Trifluoroacetic acid |
| THF | Tetrahydrofuran |
| YMC | The YMC Company, Japan |

Example 1

Preparation of Exemplary Compounds

Exemplary compounds 3 and 4:

3: 2-[4-(4-Fluorophenoxy)benzenesulfonyl]-6-[3-(4-methylpiperazin-1-yl)propoxy]-1,2,3,4-tetrahydroisoquinoline-1-carboxylic acid hydroxamide;

4: 2-[4-(4-Fluorophenoxy)benzenesulfonyl]-6-[3-(4-methylpiperazin-1-yl)propoxy]-1,2,3,4-tetrahydroisoquinoline-1-carboxylic acid;

3A: 4-Fluorophenoxybenzenesulfonyl chloride;

16.1 g (0.138 mol) of chlorosulfonic acid are slowly added dropwise to a solution of 13.05 g of 4-fluorophenoxybenzene (0.069 mol) cooled to 0° C. After the addition is complete, the mixture is stirred at room temperature for a further 4 hours. For work up, 50 ml of dichloromethane are added, and the mixture is washed once with $H_2O$. The aqueous phase is separated off and extracted twice more with 50 ml of dichloromethane each time. The combined organic phases are dried with $MgSO_4$ and concentrated, resulting in the title compound as a colorless solid. Yield: 11.03 g; 60%.

3B: Methyl 2-[4-(4-fluorophenoxy)benzenesulfonyl]-6-hydroxy-1,2,3,4-tetrahydro-isoquinoline-1-carboxylate;

A solution of 360 mg (1.7 mmol) of methyl 6-hydroxytetrahydroisoquinoline-1-carboxylate hydrochloride in 5 ml of pyridine is mixed at 0° C. with 512 mg (1.95 mmol) of 4-fluorophenoxybenzenesulfonyl chloride. The solution is stirred at room temperature for 18 hours and then the solvent is removed, The residue is taken up in ethyl acetate and washed three times with saturated $NH_4Cl$ solution, dried with $MgSO_4$ and concentrated, allowing the title compound to be isolated as a yellow solid, yield 98%.

3C: Methyl 2-[4-(4-fluorophenoxy)benzenesulfonyl]-6-[3-(4-methylpiperazin-1-yl)propoxy]-1,2,3,4-tetrahydroisoquinoline-1-carboxylate;

250 mg (0.55 mmol) of methyl 2-[4-(4-fluorophenoxy)benzenesulfonyl]-6-hydroxy-1,2,3,4-tetrahydroisoquinoline-1-carboxlate are dissolved in 5 ml of THF. At room temperature, 216 mg (0.825 mmol) of triphenylphosphine, 142 µl (0.825 mmol) of DEAD and 120 mg (0.825 mmol) of 3-(4-methylpiperazin-1-yl)propan-1-ol are added, and the solution is stirred at room temperature for 18 hours. The solvent is then removed, and the residue is chromatographed on silica gel, allowing the desired product to be isolated as a colorless solid. Yield 76%.

3: 2-[4-(4-Fluorophenoxy)benzenesulfonyl]-6-[3-(4-methylpiperazin-1-yl)propoxy]-1,2,3,4-tetrahydroisoquinoline-1-carboxylic acid hydroxamide;

4: 2-[4-(4-Fluorophenoxy)benzenesulfonyl]-6-[3-(4-methylpiperazin-1-yl)propoxy]-1,2,3,4-tetrahydroisoquinoline-1-carboxylic acid;

A solution of 61 mg (0.88 mmol) of hydroxylamine hydrochloride in 1 ml of $H_2O$ is mixed with a solution of 56 mg (1.4 mmol) of NaOH in 0.5 ml of $H_2O$ and stirred for 10 minutes. At 0° C., a solution of 240 mg (0.4 mmol) of methyl 2-[4-(4-fluorophenoxy)-benzenesulfonyl]-6-[3-(4-methylpiperazin-1-yl)propoxy]-1,2,3,4-tetrahydroisoquinoline-1-carboxylate in 0.5 ml of dioxane is added, and the mixture is stirred at 0° C. To achieve complete conversion, 61 mg (0.88 mmol) of hydroxylamine hydrochloride and 56 mg (1.4 mmol) of NaOH are added twice more. For work up, the mixture is neutralized with 1 N HCl and extracted with ethyl acetate. The organic phase is separated off, dried with $MgSO_4$ and concentrated. Chromatography of the residue on silica gel affords the hydroxamic acid (exemplary compound 3) as colorless solid in 46% yield, and the carboxylic acid (exemplary compound 4), likewise as colorless solid in a yield of 15%.

Exemplary compounds 1 and 2:

1: 2-[4-(4-Fluorophenoxy)benzenesulfonyl]-6-(2-piperidin-1-ylethoxy)-1,2,3,4-tetrahydroisoquinoline-1-carboxylic acid hydroxamide;

2: 2-[4-(4-Fluorophenoxy)benzenesulfonyl]-6-(2-piperidin-1-ylethoxy)-1,2,3,4-tetrahydroisoquinoline-1-carboxylic acid;

1A: Methyl 2-[4-(4-fluorophenoxy)benzenesulfonyl]-6-(2-piperidin-1-ylethoxy)-1,2,3,4-tetrahydroisoquinoline-1-carboxylate;

Methyl 2-[4-(4-fluorophenoxy)benzenesulfonyl]-6-hydroxy-1,2,3,4-tetrahydro-isoquinoline-1-carboxylate (3B) is reacted with 2-piperidin-4-ylethanol by the method described under 3C.

1: 2-[4-(4-Fluorophenoxy)benzenesulfonyl]-6-(2-piperidin-1-ylethoxy)-1,2,3,4-tetrahydroisoquinoline-1-carboxylic acid hydroxamide;

2: 2-[4-(4-Fluorophenoxy)benzenesulfonyl]-6-(2-piperidin-1-ylethoxy)-1,2,3,4-tetrahydroisoquinoline-1-carboxylic acid;

The title compounds are prepared starting from methyl 2-[4-(4-fluorophenoxy)benzene-sulfonyl]-6-(2-piperidin-1-ylethoxy)-1,2,3,4-tetrahydroisoquinoline-1-carboxylate by the method described for exemplary compounds ¾.

Exemplary compounds 5 and 6:

5: 2-[4-(4-Fluorophenoxy)benzenesulfonyl]-6-(2-methoxyethoxy)-1,2,3,4-tetrahydroisoquinoline-1-carboxylic acid hydroxyamide;

6: 2-[4-(4-Fluorophenoxy)benzenesulfonyl]-6-(2-methoxyethoxy)-1,2,3,4-tetrahydroisoquinoline-1-carboxylic acid;

5A: Methyl 2-[4-(4-fluorophenoxy)benzenesulfonyl]-6-(2-methoxyethoxy)-1,2,3,4-tetrahydroisoquinoline-1-carboxylate;

Methyl 2-[4-(4-fluorophenoxy)benzenesulfonyl]-6-hydroxy-1,2,3,4-tetrahydro-isoquinoline-1-carboxylate (3B) is reacted with 2-methoxyethanol by the method described under 3C.

5: 2-[4-(4-Fluorophenoxy)benzenesulfonyl]-6-(2-methoxyethoxy)-1,2,3,4-tetrahydroisoquinoline-1-carboxylic acid hydroxyamide;

6: 2-[4-(4-Fluorophenoxy)benzenesulfonyl]-6-(2-methoxyethoxy)-1,2,3,4-tetrahydroisoquinoline-1-carboxylic acid;

The title compounds are prepared starting from methyl 2-[4-(4-fluorophenoxy)benzene-sulfonyl]-6-(2-methoxyethoxy)-1,2,3,4-tetrahydroisoquinoline-1-carboxylate by the method described for exemplary compounds ¾.

Exemplary compounds 7 and 8:

7: 2-[4-(4-Fluorophenoxy)benzenesulfonyl]-6-(2-morpholin-4-ylethoxy)-1,2,3,4-tetrahydroisoquinoline-1-carboxylic acid hydroxyamide;

8: 2-[4-(4-Fluorophenoxy)benzenesulfonyl]-6-(2-morpholin-4-ylethoxy)-1,2,3,4-tetrahydroisoquinoline-1-carboxylic acid;

7A: Methyl 2-[4-(4-fluorophenoxy)benzenesulfonyl]-6-(2-morpholin-4-ylethoxy)-1,2,3,4-tetrahydroisoquinoline-1-carboxylate;

667 mg (2.0 mmol) of polymer-bound $PPh_3$ (3 mmol/g) are introduced into 2 ml of THF and, at room temperature, 229 mg (0.5 mmol) of methyl 2-[4-(4-fluorophenoxy)-benzenesulfonyl]-6-hydroxy-1,2,3,4-tetrahydroisoquinoline-1-carboxylate (3B), 242 µl (2.0 mmol) of 2-morpholin-4-ylethanol and 311 µl (2.0 mmol) of DEAD are added. After one hour, the mixture is filtered and the filtrate is concentrated in vacuo. The residue is chromatographed on silica gel (dichloromethane→dichloromethane/methanol 98:2), resulting in 53% of the title compound.

8: 2-[4-(4-Fluorophenoxy)benzenesulfonyl]-6-(2-morpholin-4-ylethoxy)-1,2,3,4-tetrahydroisoquinoline-1-carboxylic acid;

86 mg (0.15 mmol) of methyl 2-[4-(4-fluorophenoxy)benzenesulfonyl]-6-(2-morpholin-4-ylethoxy)-1,2,3,4-tetrahydroisoquinoline-1-carboxylate are heated in 15 ml of 6 N HCl to 70° C. After one hour, the mixture is allowed to cool to room temperature and neutralized with 5 N NaOH. The aqueous solution is extracted with ethyl acetate, and the organic phase is dried with $MgSO_4$ and concentrated, allowing the carboxylic acid to be isolated in a yield of 75%.

7B: 2-[4-(4-Fluorophenoxy)benzenesulfonyl]-6-(2-morpholin-4-ylethoxy)-1,2,3,4-tetrahydroisoquinoline-1-carboxylic acid (tetrahydropyran-2-yloxy)amide;

A solution of 40 mg (0.264 mmol) of HOBt and 51 mg (0.264 mmol) of EDC in 2 ml of DMF was added dropwise to a solution of 98 mg (0.176 mmol) of 2-[4-(4-fluoro-phenoxy)benzenesulfonyl]-6-(2-morpholin-4-ylethoxy)-1,2,3,4-tetrahydroisoquinoline-1-carboxylic acid and 46 mg (0.325 mmol) of O-(tetrahydropyran-2-yl)hydroxylamine in 3 ml of DMF at 0° C., and the mixture was stirred at room temperature. After standing overnight, it was poured onto $H_2O$ and extracted with ethyl acetate. The organic phase was dried with $MgSO_4$ and concentrated. The residue was chromatographed on silica gel (dichloromethane→dichloromethane/methanol 99:1), the title compound being isolated as a colorless solid. Yield: 80%.

7: 2-[4-(4-Fluorophenoxy)benzenesulfonyl]-6-(2-morpholin-4-ylethoxy)-1,2,3,4-tetrahydroisoquinoline-1-carboxylic acid hydroxyamide;

93 mg (0.141 mmol) of 2-[4-(4-fluorophenoxy)benzenesulfonyl]-6-(2-morpholin-4-ylethoxy)-1,2,3,4-tetrahydroisoquinoline-1-carboxylic acid (tetrahydropyran-2-yloxy)amide were mixed with 40 mg (0.212 mmol) of p-toluenesulfonic acid in 5 ml of methanol and stirred at room temperature. After three hours, the solvent was removed and the residue was partitioned between $H_2O$ and ethyl acetate.

The organic phase was isolated, dried with $MgSO_4$ and concentrated. The residue was chromatographed on silica gel (dichloromethane→dichloromethane/methanol 1:1), allowing the title compound to be isolated as a colorless solid after trituration with diisopropyl ether. Yield 25%.

Exemplary compounds 9 and 10:

9: 6-(2-Diethylaminoethoxy)-2-[4-(4-fluorophenoxy)benzenesulfonyl]-1,2,3,4-tetrahydroisoquinoline-1-carboxylic acid hydroxyamide;

10: 6-(2-Diethylaminoethoxy)-2-[4-(4-fluorophenoxy)benzenesulfonyl]-1,2,3,4-tetrahydroisoquinoline-1-carboxylic acid;

9A: Methyl 6-(2-diethylaminoethoxy)-2-[4-(4-fluorophenoxy)benzenesulfonyl]-1,2,3,4-tetrahydroisoquinoline-1-carboxylate;

Methyl 2-[4-(4-fluorophenoxy)benzenesulfonyl]-6-hydroxy-1,2,3,4-tetrahydro-isoquinoline-1-carboxylate (3B) is reacted with 2-diethylaminoethanol by the method described under 3C.

10: 6-(2-Diethylaminoethoxy)-2-[4-(4-fluorophenoxy)benzenesulfonyl]-1,2,3,4-tetrahydroisoquinoline-1-carboxylic acid;

Methyl 6-(2-diethylaminoethoxy)-2-[4-(4-fluorophenoxy)benzenesulfonyl]-1,2,3,4-tetrahydroisoquinoline-1-carboxylate is subjected to acid hydrolysis in analogy to the method described under 8.

9: 6-(2-Diethylaminoethoxy)-2-[4-(4-fluorophenoxy)benzenesulfonyl]-1,2,3,4-tetrahydroisoquinoline-1-carboxylic acid hydroxyamide;

6-(2-Diethylaminoethoxy)-2-[4-(4-fluorophenoxy)benzenesulfonyl]-1,2,3,4-tetrahydro-isoquinoline-1-carboxylic acid is converted into the desired hydroxamic acid by the method described under 19.

Exemplary compounds 11 and 12:

11: 2-[4-(4-Fluorophenoxy)benzenesulfonyl]-6-(2-imidazol-1-ylethoxy)-1,2,3,4-tetrahydroisoquinoline-1-carboxylic acid hydroxyamide;

12: 2-[4-(4-Fluorophenoxy)benzenesulfonyl]-6-(2-imidazol-1-ylethoxy)-1,2,3,4-tetrahydroisoquinoline-1-carboxylic acid;

11A: Methyl 2-[4-(4-fluorophenoxy)benzenesulfonyl]-6-(2-imidazol-1-ylethoxy)-1,2,3,4-tetrahydroisoquinoline-1-carboxylate;

Methyl 2-[4-(4-fluorophenoxy)benzenesulfonyl]-6-hydroxy-1,2,3,4-tetrahydro-isoquinoline-1-carboxylate (3B) is reacted with 2-imidazol-1-ylethanol by the method described under 3C.

12: 2-[4-(4-Fluorophenoxy)benzenesulfonyl]-6-(2-imidazol-1-ylethoxy)-1,2,3,4-tetrahydroisoquinoline-1-carboxylic acid;

Methyl 2-[4-(4-fluorophenoxy)benzenesulfonyl]-6-(2-imidazol-1-ylethoxy)-1,2,3,4-tetrahydroisoquinoline-1-carboxylate is subjected to acid hydrolysis by the method described under 8.

11: 2-[4-(4-Fluorophenoxy)benzenesulfonyl]-6-(2-imidazol-1-ylethoxy)-1,2,3,4-tetrahydroisoquinoline-1-carboxylic acid hydroxyamide;

2-[4-(4-Fluorophenoxy)benzenesulfonyl]-6-(2-imidazol-1-ylethoxy)-1,2,3,4-tetrahydro-isoquinoline-1-carboxylic acid is converted into the desired hydroxamic acid by the method described under 19.

Exemplary compounds 13 and 14:

13: 2-[4-(4-Methoxyphenoxy)benzenesulfonyl]-6-(2-piperidin-1-ylethoxy)-1,2,3,4-tetrahydroisoquinoline-1-carboxylic acid hydroxyamide;

14: 2-[4-(4-Methoxyphenoxy)benzenesulfonyl]-6-(2-piperidin-1-ylethoxy)-1,2,3,4-tetrahydroisoquinoline-1-carboxylic acid;

13A: 4-(4-Methoxyphenoxy)benzenesulfonyl chloride;

The title compound is prepared by process known from the literature by chlorosulfonation of 4-methoxybiphenyl ether (U.S. Pat. No. 6,153,757).

13B: Methyl 6-hydroxy-2-[4-(4-methoxyphenoxy)benzenesulfonyl]-1,2,3,4-tetrahydro-isoquinoline-1-carboxylate;

4-(4-Methoxyphenoxy)benzenesulfonyl chloride is reacted with methyl 6-hydroxytetra-hydroisoquinoline-1-carboxylate hydrochloride in analogy to the method described in 3B to give the desired sulfonamide.

13C: Methyl 2-[4-(4-methoxyphenoxy)benzenesulfonyl]-6-(2-piperidin-1-ylethoxy)-1,2,3,4-tetrahydroisoquinoline-1-carboxylate;

Methyl 6-hydroxy-2-[4-(4-methoxyphenoxy)benzenesulfonyl]-1,2,3,4-tetrahydroiso-quinoline-1-carboxylate is reacted with 2-piperidin-1-ylethanol in analogy to the method described under 3C.

13: 2-[4-(4-Methoxyphenoxy)benzenesulfonyl]-6-(2-piperidin-1-ylethoxy)-1,2,3,4-tetrahydroisoquinoline-1-carboxylic acid hydroxyamide;

14: 2-[4-(4-Methoxyphenoxy)benzenesulfonyl]-6-(2-piperidin-1-ylethoxy)-1,2,3,4-tetrahydroisoquinoline-1-carboxylic acid;

The title compounds are prepared starting from methyl 2-[4-(4-methoxyphenoxy)-benzenesulfonyl]-6-(2-piperidin-1-ylethoxy)-1,2,3,4-tetrahydroisoquinoline-1-carboxylate by the method described for exemplary compounds ¾.

Exemplary compounds 15 and 16:

15: 6-(2-Diethylaminoethoxy)-2-[4-(4-methoxyphenoxy)benzenesulfonyl]-1,2,3,4-tetrahydroisoquinoline-1-carboxylic acid hydroxyamide;

16: 6-(2-Diethylaminoethoxy)-2-[4-(4-methoxyphenoxy)benzenesulfonyl]-1,2,3,4-tetrahydroisoquinoline-1-carboxylic acid;

15A: Methyl 6-(2-diethylaminoethoxy)-2-[4-(4-methoxyphenoxy)benzenesulfonyl]-1,2,3,4-tetrahydroisoquinoline-1-carboxylate;

Methyl 6-hydroxy-2-[4-(4-methoxyphenoxy)benzenesulfonyl]-1,2,3,4-tetrahydroiso-quinoline-1-carboxylate (13B) is reacted with 2-diethylaminoethanol by the method described under 3C.

15: 6-(2-Diethylaminoethoxy)-2-[4-(4-methoxyphenoxy)benzenesulfonyl]-1,2,3,4-tetrahydroisoquinoline-1-carboxylic acid hydroxyamide;

16: 6-(2-Diethylaminoethoxy)-2-[4-(4-methoxyphenoxy)benzenesulfonyl]-1,2,3,4-tetrahydroisoquinoline-1-carboxylic acid;

The title compounds are prepared starting from methyl 6-(2-diethylaminoethoxy)-2-[4-(4-methoxyphenoxy)benzenesulfonyl]-1,2,3,4-tetrahydroisoquinoline-1-carboxylate by the method described for exemplary compounds ¾.

Exemplary compounds 17 and 18:

17: 6-(2-Imidazol-1-ylethoxy)-2-[4-(4-methoxyphenoxy)benzenesulfonyl]-1,2,3,4-tetrahydroisoquinoline-1-carboxylic acid hydroxyamide;

18: 6-(2-Imidazol-1-ylethoxy)-2-[4-(4-methoxyphenoxy)benzenesulfonyl]-1,2,3,4-tetrahydroisoquinoline-1-carboxylic acid;

17A: Methyl 6-(2-imidazol-1-ylethoxy)-2-[4-(4-methoxyphenoxy)benzenesulfonyl]-1,2,3,4-tetrahydroisoquinoline-1-carboxylate;

Methyl 6-hydroxy-2-[4-(4-methoxyphenoxy)benzenesulfonyl]-1,2,3,4-tetrahydroiso-quinoline-1-carboxylate (13B) is reacted with 2-imidazol-1-ylethanol in analogy to the method described under 3C.

17: 6-(2-Imidazol-1-ylethoxy)-2-[4-(4-methoxyphenoxy)benzenesulfonyl]-1,2,3,4-tetrahydroisoquinoline-1-carboxylic acid hydroxyamide;

18: 6-(2-Imidazol-1-ylethoxy)-2-[4-(4-methoxyphenoxy)benzenesulfonyl]-1,2,3,4-tetrahydroisoquinoline-1-carboxylic acid;

The title compounds are prepared starting from 6-(2-imidazol-1-ylethoxy)-2-[4-(4-methoxyphenoxy)benzenesulfonyl]-1,2,3,4-tetrahydroisoquinoline-1-carboxylic acid by the method described for exemplary compounds ¾.

Exemplary compounds 19 and 20:

19: 2-[4-(4-Fluorophenoxy)benzenesulfonyl]-5-(2-piperidin-1-ylethoxy)-1,2,3,4-tetrahydroisoquinoline-1-carboxylic acid hydroxyamide;

20: 2-[4-(4-Fluorophenoxy)benzenesulfonyl]-5-(2-piperidin-1-yiethoxy)-1,2,3,4-tetrahydroisoquinoline-1-carboxylic acid;

19A: 4-(4-Fluorophenoxy)-N-[2-(2-methoxyphenyl)ethyl]benzenesulfonamide;

0.256 ml (1.74 mmol) of ortho-methoxyphenethylamine and 0.243 ml (1.74 mmol) of triethylamine are dissolved in 20 ml of THF and, at room temperature, a solution of 500 mg (1.74 mmol) of 4-fluorophenoxybenzenesulfonyl chloride (3A) in 10 ml of THF is added. After stirring at room temperature for one hour the resulting salts are removed by filtration and the filtrate is concentrated in vacuo, allowing the title compound to be isolated in a yield of 89%.

19B: 4-(4-Fluorophenoxy)-N-[2-(2-hydroxyphenyl)ethyl]benzenesulfonamide;

620 mg (1.54 mmol) of 4-(4-fluorophenoxy)-N-[2-(2-methoxyphenyl)ethyl]benzene-sulfonamide are dissolved in 10 ml of dichloromethane and, at −40° C., 3.09 ml (3.09 mmol) of a 1 M solution of boron tribromide in dichloromethane are added. The solution is warmed to room temperature and stirred for a further four hours. It is subsequently added to water, the phases are separated, and the organic phase is washed twice more with $H_2O$. The dichloromethane phase is dried with $MgSO_4$ and concentrated, allowing the desired phenol to be isolated as a brown oil. Crude yield 89%.

19C: 4-(4-Fluorophenoxy)-N-{2-[2-(2-piperidin-1-ylethoxy)phenyl]ethyl}benzene-sulfonamide;

200 mg (0.516 mmol) of 4-(4-fluorophenoxy)-N-[2-(2-hydroxyphenyl)ethyl]benzene-sulfonamide are reacted in 20 ml of THF with 230 mg (0.878 mmol) of triphenyl-phosphine, 141 μl (0.774 mmol) of DEAD and 0.165 ml (1.239 mmol) of 2-piperidin-1-ylethanol in analogy to the method described under 3C, resulting in the title compound in a yield of 69%.

20: 2-[4-(4-Fluorophenoxy)benzenesulfonyl]-5-(2-piperidin-1-ylethoxy)-1,2,3,4-tetra-hydroisoquinoline-1-carboxylic acid;

110 mg (0.221 mmol) of 4-(4-fluorophenoxy)-N-{2-[2-(2-piperidin-1-ylethoxy)phenyl]-ethyl}benzenesulfonamide are stirred together with 49.1 µl (0.441 mmol) of glyoxylic acid (50% strength in $H_2O$) in 5 ml of trifluoroacetic acid at room temperature. After standing overnight, the mixture is concentrated in vacuo and the residue is chromatographed on silica gel, resulting in the desired carboxylic acid in a yield of 52%.

19: 2-[4-(4-Fluorophenoxy)benzenesulfonyl]-5-(2-piperidin-1-ylethoxy)-1,2,3,4-tetra-hydroisoquinoline-1-carboxylic acid hydroxyamide;

8.16 µl (85.6 µmol) of ethyl chloroformate are added to a solution of 38 mg (68.5 µmol) of 2-[4-(4-fluorophenoxy)benzenesulfonyl]-5-(2-piperidin-1-ylethoxy)-1,2,3,4-tetra-hydroisoquinoline-1-carboxylic acid and 16.6 µl (151 µmol) of N-methylmorpholine in 2 ml of DMF at −20° C., and the mixture is stirred at −20° C. for 30 minutes. Then 37.2 µl (274 µmol) of O-trimethylsilylhydroxylamine are added, and the solution is warmed slowly to room temperature. After standing overnight, it is concentrated in vacuo and the residue is purified by chromatography on silica gel, allowing the title compound to be isolated as a colorless solid. Yield 46%.

Exemplary compounds 21 and 22:

21: 8-Bromo-2-[4-(4-fluorophenoxy)benzenesulfonyl]-5-(2-piperidin-1-ylethoxy)-1,2,3,4-tetrahydroisoquinoline-1-carboxylic acid hydroxyamide;

22: 8-Bromo-2-[4-(4-fluorophenoxy)benzenesulfonyl]-5-(2-piperidin-1-ylethoxy)-1,2,3,4-tetrahydroisoquinoline-1-carboxylic acid;

21A: N-[2-(5-Bromo-2-methoxyphenyl)ethyl]-4-(4-fluorophenoxy)benzenesulfonamide;

1.0 g (3.2 mmol) of 5-bromo-2-methoxyphenylethylamine hydrochloride is introduced together with 1.25 g (9.6 mmol) of Hünig's base into 10 ml of dichloromethane and, at 0° C., a solution of 1.02 g (3.5 mmol) of 4-(4-fluorophenoxy)benzenesulfonyl chloride in 10 ml of dichloromethane is added, and the mixture is stirred at room temperature for four hours. For workup, it is diluted with about 30 ml of dichloromethane and washed with 2 N HCl, 1 N NaOH and with $H_2O$. The organic phase is dried with $MgSO_4$ and concentrated. The crude product obtained in this way can be reacted further without further purification.

21B: 8-Bromo-2-[4-(4-fluorophenoxy)benzenesulfonyl]-5-methoxy-1,2,3,4-tetrahydro-isoquinoline-1-carboxylic acid;

0.81 g (1.7 mmol) of N-[2-(5-bromo-2-methoxyphenyl)ethyl]-4-(4-fluorophenoxy)-benzenesulfonamide (crude product, 21A) is stirred with 0.32 g (3.4 mmol) of glyoxylic acid monohydrate in 10 ml of trifluoroacetic acid at room temperature. After 12 hours, the mixture is poured onto ice and extracted with dichloromethane. Drying with $MgSO_4$ and concentration result in 0.84 g of the title compound which can be reacted further without further purification.

21C: 8-Bromo-2-[4-(4-fluorophenoxy)benzenesulfonyl]-5-hydroxy-1,2,3,4-tetrahydro-isoquinoline-1-carboxylic acid;

0.84 g (1.6 mmol) of 8-bromo-2-[4-(4-fluorophenoxy)benzenesulfonyl]-5-methoxy-1,2,3,4-tetrahydroisoquinoline-1-carboxylic acid (crude product, 21B) are dissolved in 20 ml of dichloromethane. At 0° C., a solution of 1.19 g (4.7 mmol) of boron tribromide in 10 ml of dichloromethane is added dropwise, and the solution is allowed slowly to reach room temperature. After two hours, it is washed twice with 2 N HCl and once with $H_2O$, dried with $MgSO_4$ and freed of solvent, resulting in 0.61 g of the title compound which can be reacted further without further purification.

21D: Ethyl 8-bromo-2-[4-(4-fluorophenoxy)benzenesulfonyl]-5-hydroxy-1,2,3,4-tetrahydroisoquinoline-1-carboxylate;

0.60 g (1.2 mmol) of 8-bromo-2-[4-(4-fluorophenoxy) benzenesulfonyl]-5-hydroxy-1,2,3,4-tetrahydroisoquinoline-1-carboxylic acid (crude product, 21C) are mixed with 0.25 ml of conc. $H_2SO_4$ in 10 ml of ethanol and heated to reflux. After five hours, a further 0.25 ml of conc. $H_2SO_4$ is added, and heating to reflux is continued for one hour. For workup, the mixture is concentrated, and the residue is taken up in sat. $Na_2CO_3$ solution and extracted twice with dichloromethane. The organic phases are dried with $MgSO_4$, and the solvent is removed in vacuo. The crude product obtained in this way can be reacted further without purification.

21E: Ethyl 8-bromo-2-[4-(4-fluorophenoxy)benzenesulfonyl]-5-(2-piperidin-1-ylethoxy)-1,2,3,4-tetrahydroisoquinoline-1-carboxylate;

0.515 g of $PPh_3$ (polymer-bound, 1.2-1.5 mmol/g) are mixed with 0.13 g of diisopropyl azodicarboxylate in 5 ml of dichloromethane and shaken at room temperature for 15 min. Then 0.17 g (0.31 mmol) of ethyl 8-bromo-2-[4-(4-fluorophenoxy)benzene-sulfonyl]-5-hydroxy-1,2,3,4-tetrahydroisoquinoline-1-carboxylate (crude product, 21D), 0.031 g (0.31 mmol) of triethylamine and 0.04 g (0.31 mmol) of 2-piperidin-1-ylethanol are added, and the mixture is shaken at room temperature until no further increase in conversion can be detected by means of an LCMS check. For workup, the mixture is filtered and the filtrate is washed twice with $H_2O$. The aqueous phases are extracted twice with dichloromethane. The combined organic phases dried with $MgSO_4$ and evaporated. The crude product obtained in this way is purified by prep. HPLC, resulting in 0.08 g of the title compound as trifluoroacetate.

22: 8-Bromo-2-[4-(4-fluorophenoxy)benzenesulfonyl]-5-(2-piperidin-1-ylethoxy)-1,2,3,4-tetrahydroisoquinoline-1-carboxylic acid;

0.25 g (0.38 mmol) of ethyl 8-bromo-2-[4-(4-fluorophenoxy)benzenesulfonyl]-5-(2-piperidin-1-ylethoxy)-1,2,3,4-tetrahydroisoquinoline-1-carboxylate are mixed with 2 ml of 2 N KOH in 7 ml of methanol and stirred at room temperature. After two hours, a further 2 ml of 2 N KOH are added, and stirring is continued for one hour. For workup, the methanol is removed in a rotary evaporator and the aqueous residue is adjusted to a pH of 6-7 with 2 N HCl. The precipitate is filtered off with suction and dried to afford 0.13 g of the desired carboxylic acid.

21: 8-Bromo-2-[4-(4-fluorophenoxy)benzenesulfonyl]-5-(2-piperidin-1-ylethoxy)-1,2,3,4-tetrahydroisoquinoline-1-carboxylic acid hydroxyamide;

0.1 g (0.16 mmol) of 8-bromo-2-[4-(4-fluorophenoxy) benzenesulfonyl]-5-(2-piperidin-1-ylethoxy)-1,2,3,4-tetrahydroisoquinoline-1-carboxylic acid is converted into the desired hydroxamic acid 21 by the method described for example 19, resulting in the title compound as trifluoroacetate after purification by prep. HPLC.

Exemplary compound 23:

23: 5-(2-Piperidin-1-ylethoxy)-2-toluene-4-sulfonyl)-1,2,3,4-tetrahydroisoquinoline-1-carbohydroxamic acid;

23A: N-[2-(2-Methoxyphenyl)-ethyl]-4-methylbenzenesulfonamide;

5.0 g (33 mmol) of ortho-methoxyphenethylamine are reacted with 1.2 equivalents of para-toluenesulfonyl chloride in analogy to the method described under 19A, resulting in the title compound in virtually quantitative yield.

23B: N-[2-(2-Hydroxyphenyl)ethyl]-4-methylbenzenesulfonamide;

The title compound is prepared starting from N-[2-(2-methoxyphenyl)ethyl]-4-methylbenzenesulfonamide in analogy to the method described under 19B, it likewise being possible for the crude product to be reacted further without further purification.

23C: 4-Methyl-N-{2-[2-(2-piperidin-1-yiethoxy)phenyl]ethyl}benzenesulfonamide;

N-[2-(2-Hydroxyphenyl)ethyl]-4-methylbenzenesulfonamide is reacted with 2-piperidin-1-ylethanol by the method described under 3C. Yield 69%.

23D: 5-(2-Piperidin-1-ylethoxy)-2-(toluene-4-sulfonyl)-1,2,3,4-tetrahydroisoquinoline-1-carboxylic acid;

4-Methyl-N-{2-[2-(2-piperidin-1-ylethoxy)phenyl]ethyl}benzenesulfonamide is reacted with glyoxylic acid in analogy to the method described for Example 20.

23: 5-(2-Piperidin-1-ylethoxy)-2-toluene-4-sulfonyl)-1,2,3,4-tetrahydroisoquinoline-1-carbohydroxamic acid;

The desired hydroxamic acid is prepared starting from 5-(2-piperidin-1-yiethoxy)-2-(toluene-4-sulfonyl)-1,2,3,4-tetrahydroisoquinoline-1-carboxylic acid in analogy to the method indicated for Example 19.

Example 2

Catalytic Inhibition of Gelatinase B (MMP-9) in Human Serum by Synthetic MMP Inhibitors Freshly isolated human serum was shock-frozen in the desired volume in liquid $N_2$ and then stored at −80° C. For the catalytic inhibition of MMP-9 in human serum, the appropriate parts by volume of human serum were thawed at room temperature. 100 parts by volume of undiluted, freshly thawed human serum were mixed with 1 part by volume of test substance, thoroughly mixed and incubated at 37° C. for 1 h. The test substances were dissolved in 100% dimethyl sulfoxide, and a 10 mM stock solution was prepared. For dose-effect plots, the test substances were tested in final concentrations of from 200 μM to 0.001 μM for their catalytic inhibition of MMP-9 in human serum. The final concentration of DMSO in the reaction solution was 1% in each case.

Active MMP-9 from the reaction solutions described above was determined with the aid of a MMP-9 activity assay system (Amersham Pharmacia Biotech Europe GmbH).

After the incubation, one part by volume of the reaction mixture described above was diluted with 20 parts by volume of MMP-9 reaction buffer. The samples diluted in this way were transferred to a 96-well assay plate (Amersham Pharmacia Biotech Europe GmbH, Germany) coated with a specific MMP-9 antibody and incubated at 4° C. overnight. In addition, various concentrations of dissolved, recombinant human pro MMP-9 were likewise transferred onto the 96-well assay plate to construct the standard curve.

100 μl of the respective samples were employed per well. All the MMP-9 present in the samples (proMMP-9; active MMP-9 complexed or not complexed with the respective test substance) was isolated from the sample mixture by the specific MMP-9 antibody and bound to a solid matrix.

The immobilized MMP-9 samples were, after the incubation, washed 4× with 200 μl of washing buffer each time.

Subsequently, proMMP-9 present was activated with 50 μl of APMA solution at 37° C. for 1.5 h.

The enzymic activity was measured by adding, after the incubation, 50 μl of detection reagent to each sample and mixing. The absorption of the assay plate charged in this way was measured immediately at 405 nm in an ELISA measuring instrument in order to fix time t=0. The assay plate was then incubated at 37° C. for 2 to 3 h and thereafter the absorption at 405 nm was measured.

Using the standard curve employed, the resulting measurements were converted as follows to the remaining, uninhibited active form of MMP-9 in ng/ml.

$X=(Y-b)/m*20$
X=active MMP-9 in [ng/mL]
Y=measured absorption
b=intercept on y axis
m=gradient
20=dilution factor The inhibitory effect was calculated as percentage inhibition by the following formula: % inhibition=$100-(X_2*100/X_1)$ $X_1$=active MMP-9 in [ng/ml] without test substance
$X_2$=active MMP-9 in [ng/ml] with test substance The $IC_{50}$, the concentration of inhibitor which is necessary for 50% inhibition of the enzymic activity, was determined graphically by plotting the percentage inhibitions at various inhibitor concentrations.

The composition of the buffer solutions respectively employed was as follows:
Reaction buffer:
50 mM Tris-HCl pH 7.6
1.5 mM NaCl
0.5 mM $CaCl_2$
1 μM $ZnCl_2$
0.01% (v/v) BRIJ 35
Recombinant MMP-9 employed for standard:
0; 0.5; 1.0; 2.0; 4.0; 8.0; 16.0 ng/ml
Washing buffer:
0.01 M sodium phosphate buffer pH 7.0
0.05% Tween20
APMA solution:
1 mM p-aminophenyl mercuric acetate
50 mM Tris-HCl pH 7.6
1.5 mM NaCl
0.5 mM $CaCl_2$
1 μM $ZnCl_2$
0.01% (v/v) BRIJ 35
Detection reagent:
Modified urokinase
S-2444 peptide substrate
50 mM Tris-HCl pH 7.6
1.5 mM NaCl
0.5 mM $CaCl_2$
1 μM $ZnCl_2$
0.01% (v/v) BRIJ 35

Example 3

Determination of the Solubility by Means of a CLND (Chemo Luminescence Nitrogen Detector)

For the thermodynamic solubility measurement, 1 mg of solid substance is taken up in 250 μl of PBS buffer (sodium phosphate 10 mM; pH 7.4; 0.9% NaCl isotonic salt concentration) and mixed, and the suspension is shaken at room temperature for 16 hours. The solution is then centrifuged at 14 000 rpm for 5 minutes. The solution is removed from the pellet and filtered through a syringe filter (0.45 μm pore size). The presence of a pellet is checked in order to ensure that a saturated solution was present. The filtered clear solution is analyzed by HPLC.

The dissolved amount of substance is quantified using a generic chromatographic method:

Either a calibration line derived from DMSO stock solutions (1-500 μM) of the appropriate substance is used to quantify the corresponding signal in the UV (254 nm) chromatogram of the solubility sample, or the quantification is undertaken via the peak area in the CLND trace. In the case of CLND quantification, caffeine is used as standard in a calibrating dilution.

The limit of quantitation is determined together with the calibration series. The limit of quantitation is normally 1-5 μM with UV detection, 5-10 μM with CLND quantification (depending on the number of nitrogen atoms in the molecule or the extinction coefficient of the molecule). If the intensity of the signal from the dissolved molecule is below the limit of quantitation, the result is reported as less than the limit of quantitation.

The clear solution after incubation for 16 hours is always measured as duplicates, once diluted 40-fold and once directly without dilution. The sample for which the signal is in the linear range of the calibration is used to determine the solubility.

TABLE 3

Analytical data of exemplary compounds of the formula (I)

| Exemplary comp. | Name | Retention time [min] | Mass, M + H$^+$ [g/mol] | LCMS method |
|---|---|---|---|---|
| 1 | 2-[4-(4-Fluorophenoxy)-benzenesulfonyl]-6-(2-piperidin-1-ylethoxy)-1,2,3,4-tetrahydro-isoquinoline-1-carboxylic acid hydroxyamide | 3.27 | 570.2 | A |
| 2 | 2-[4-(4-Fluorophenoxy)-benzenesulfonyl]-6-(2-piperidin-1-ylethoxy)-1,2,3,4-tetrahydro-isoquinoline-1-carboxylic acid | 1.22 | 555.2 | D |
| 3 | 2-[4-(4-Fluorophenoxy)-benzenesulfonyl]-6-[3-(4-methylpiperazin-1-yl)propoxy]-1,2,3,4-tetrahydroisoquinoline-1-carboxylic acid hydroxyamide | 2.95 | 599.3 | A |
| 4 | 2-[4-(4-Fluorophenoxy)-benzenesulfonyl]-6-[3-(4-methylpiperazin-1-yl)propoxy]-1,2,3,4-tetrahydroisoquinoline-1-carboxylic acid | 3.94 | 584.5 | B |
| 5 | 2-[4-(4-Fluorophenoxy)-benzenesulfonyl]-6-(2-methoxyethoxy)-1,2,3,4-tetrahydroisoquinoline-1-carboxylic acid hydroxyamide | 3.76 | 517.2 | A |
| 6 | 2-[4-(4-Fluorophenoxy)-benzenesulfonyl]-6-(2-methoxyethoxy)-1,2,3,4-tetrahydroisoquinoline-1-carboxylic acid | 4.09 | 502.2 | A |
| 7 | 2-[4-(4-Fluorophenoxy)-benzenesulfonyl]-6-(2-morpholin-4-ylethoxy)-1,2,3,4-tetrahydro-isoquinoline-1-carboxylic acid hydroxyamide | 3.66 | 572.5 | B |
| 8 | 2-[4-(4-Fluorophenoxy)-benzenesulfonyl]-6-(2-morpholin-4-ylethoxy)-1,2,3,4-tetrahydro-isoquinoline-1-carboxylic acid | 3.90 | 557.4 | B |
| 9 | 6-(2-Diethylaminoethoxy)-2-[4-(4-fluorophenoxy)benzenesulfonyl]-1,2,3,4-tetrahydroisoquinoline-1-carboxylic acid hydroxyamide | 3.23 | 558.1 | A |
| 10 | 6-(2-Diethylaminoethoxy)-2-[4-(4-fluorophenoxy)benzenesulfonyl]-1,2,3,4-tetrahydroisoquinoline-1-carboxylic acid | 3.89 | 543.1 | A |
| 11 | 2-[4-(4-Fluorophenoxy)-benzenesulfonyl]-6-(2-imidazol-1-ylethoxy)-1,2,3,4-tetrahydro-isoquinoline-1-carboxylic acid hydroxyamide | 3.08 | 553.0 | A |
| 12 | 2-[4-(4-Fluorophenoxy)-benzenesulfonyl]-6-(2-imidazol-1-ylethoxy)-1,2,3,4-tetrahydro-isoquinoline-1-carboxylic acid | 3.30 | 538.0 | A |

TABLE 3-continued

Analytical data of exemplary compounds of the formula (I)

| Exemplary comp. | Name | Retention time [min.] | Mass, M + H⁺ [g/mol] | LCMS method |
|---|---|---|---|---|
| 13 | 2-[4-(4-Methoxyphenoxy)-benzenesulfonyl]-6-(2-piperidin-1-ylethoxy)-1,2,3,4-tetrahydro-isoquinoline-1-carboxylic acid hydroxyamide | 3.96 | 582.6 | B |
| 14 | 2-[4-(4-Methoxyphenoxy)-benzenesulfonyl]-6-(2-piperidin-1-ylethoxy)-1,2,3,4-tetrahydro-isoquinoline-1-carboxylic acid | 4.15 | 567.5 | B |
| 15 | 6-(2-Diethylaminoethoxy)-2-[4-(4-methoxyphenoxy)benzenesulfonyl]-1,2,3,4-tetrahydroisoquinoline-1-carboxylic acid hydroxyamide | 3.19 | 570.2 | A |
| 16 | 6-(2-Diethylaminoethoxy)-2-[4-(4-methoxyphenoxy)benzenesulfonyl]-1,2,3,4-tetrahydroisoquinoline-1-carboxylic acid | 4.21 | 555.5 | B |
| 17 | 6-(2-Imidazol-1-ylethoxy)-2-[4-(4-methoxyphenoxy)benzenesulfonyl]-1,2,3,4-tetrahydroisoquinoline-1-carboxylic acid hydroxyamide | 3.12 | 565.2 | A |
| 18 | 6-(2-Imidazol-1-ylethoxy)-2-[4-(4-methoxyphenoxy)benzenesulfonyl]-1,2,3,4-tetrahydroisoquinoline-1-carboxylic acid | 4.13 | 550.4 | B |
| 19 | 2-[4-(4-Fluorophenoxy)-benzenesulfonyl]-5-(2-piperidin-1-ylethoxy)-1,2,3,4-tetrahydro-isoquinoline-1-carboxylic acid hydroxyamide | 3.19 | 570.3 | A |
| 20 | 2-[4-(4-Fluorophenoxy)-benzenesulfonyl]-5-(2-piperidin-1-ylethoxy)-1,2,3,4-tetrahydro-isoquinoline-1-carboxylic acid | 4.25 | 555.5 | B |
| 21 | 8-Bromo-2-[4-(4-fluorophenoxy)-benzenesulfonyl]-5-(2-piperidin-1-ylethoxy)-1,2,3,4-tetrahydro-isoquinoline-1-carboxylic acid hydroxyamide | 1.40 | 648.3/650.4 | C |
| 22 | 8-Bromo-2-[4-(4-fluorophenoxy)-benzenesulfonyl]-5-(2-piperidin-1-ylethoxy)-1,2,3,4-tetrahydro-isoquinoline-1-carboxylic acid | 1.53 | 633.3/635.3 | C |
| 23 | 5-(2-Piperidin-1-ylethoxy)-2-toluene-4-sulfonyl)-1,2,3,4-tetrahydroisoquinoline-1-carbohydroxamic acid | 1.10 | 474.3 | C |

LCMS Methods:

| | | |
|---|---|---|
| A | MS instrument: LCT/Ionization: ESI+; Stationary phase: Hypersil C18; Mobile phase: (ACN):(H$_2$O + 0.05% TFA), 5:95 (0 min) to 95:5 (5 min) to 95:5 (5.5 min) to 95:5 (7 min); Flow rate: 1 ml/min; Temperature: 30° C. | |
| B | MS instrument: MUX/Ionization: ESI+; Stationary phase: Atlantis C18; Mobile phase: (ACN):(H$_2$O + 0.05% TFA), 5:95 (0 min) to 95:5 (5 min) to 95:5 (5.5 min) to 95:5 (7 min); Flow rate: 1 ml/min; Temperature: 30° C. | |
| C | MS instrument: LCT/Ionization: ESI+; Stationary phase: Col YMC J'sphere 33x2; Mobile phase: (ACN + 0.05% TFA):(H$_2$O + 0.05% TFA), 5:95 (0 min) to 95:5 (2.5 min) to 95:5 (3 min); Flow rate: 1 ml/min; Temperature: 30° C. | |
| D | MS instrument: LCT/Ionization: ESI+; Stationary phase: Col YMC J'sphere ODS H80 20x2; Mobile phase: (ACN):(H$_2$O + 0.05% TFA), 4:96 (0 min) to 95:5 (2.0 min) to 95:5 (2.4 min); Flow rate: 1 ml/min; Temperature: 30° C. | |

We claim:

1. A compound of formula (I)

where $R_1$, $R_2$ and $R_3$ are independently of one another H, F, Cl, Br, I, NO$_2$, CN, OH, (C$_1$-C$_6$)alkyl, (C$_2$-C$_6$)alkenyl, (C$_3$-C$_8$)cycloalkyl, (C$_1$-C$_4$)alkylene-(C$_3$-C$_8$)cycloalkyl, (C$_3$-C$_8$)cycloalkylene-(C$_1$-C$_4$)alkyl, —O(C$_1$-C$_6$)alkyl, —O(C$_2$-C$_6$)alkenyl, —O(C$_3$-C$_8$)cycloalkyl, —O(C$_1$-C$_4$)alkylene-(C$_3$-C$_8$)cycloalkyl, —O(C$_3$-C$_8$)cycloalkylene-(C$_1$-C$_4$)alkyl, —OC(O)—(C$_1$-C$_6$)alkyl, —OC(O)—(C$_2$-C$_6$)alkenyl, —OC(O)—(C$_3$-C$_8$)cycloalkyl, —OC(O)—(C$_1$-C$_4$)alkylene-(C$_3$-C$_8$)cycloalkyl, —OC(O)—(C$_3$-C$_8$)cycloalkylene-(C$_1$-C$_4$)alkyl, —C(O)O—(C$_1$-C$_6$)alkyl, —C(O)O—(C$_2$-C$_6$)alkenyl, —C(O)O—(C$_3$-C$_8$)cycloalkyl, —C(O)O—(C$_1$-C$_4$)alkylene-(C$_3$-C$_8$)cycloalkyl, —C(O)O—(C$_3$-C$_8$)cycloalkylene-(C$_1$-C$_4$)alkyl, —C(O)NR$_5$R$_6$, —NR$_5$R$_6$, —NR$_5$C(O)R$_6$, or a group —X-Q-Y, where X is a covalent bond, O, S, NR$_7$, C(O)NR$_7$, SO$_2$ or SO$_2$NR$_7$, Q is (C$_1$-C$_4$)alkylene, CH=CH or C≡C, Y is —OR$_8$, —NR$_8$R$_9$, —C(O)OR$_8$, —S(O)$_2$OR$_8$, —SO$_2$NR$_8$R$_9$, or a five- or six-membered saturated heterocycloalkyl radical containing 1, 2, 3 or 4 ring heteroatoms selected from N or O, in which the N atoms are substituted by H or (C$_1$-C$_6$)alkyl, or Y is a five- or six-membered heteroaryl radical having 1, 2, 3 or 4 N ring atoms, where 1, 2 or 3 radicals of $R_1$, $R_2$ and $R_3$ is —X-Q-Y, A is —C(O)OR$_{10}$, —C(O)NR$_{10}$R$_{11}$, —C(O)NR$_{10}$OH or —CH$_2$SH, n is 0, 1 or 2, L is O, NH, N(C$_1$-C$_6$)alkyl, a covalent bond or (C$_1$-C$_4$) alkylene, $R_4$ is phenyl or (C$_5$-C$_{14}$)heteroaryl, where the phenyl or (C$_5$-C$_{14}$)heteroaryl radical is unsubstituted or is substituted by a group T-Z, where T is a covalent bond, O, S, O(C$_1$-C$_4$)alkylene, N(R$_{12}$), C(O), C(O)O, OC(O), C(O)N(R$_{10}$), N(R$_{12}$)—C(O) or N(R$_{12}$)—C(O)—N(R$_{13}$), Z is phenyl, (C$_5$-C$_{14}$)heteroaryl, or (C$_3$-C$_8$)heterocycloalkyl, where phenyl, (C$_5$-C$_{14}$)heteroaryl or (C$_3$-C$_8$)heterocycloalkyl is unsubstituted or is substituted by 1, 2 or 3 substituents independently of one another selected from F, Cl, Br, I, CN, OH, NO$_2$, (C$_1$-C$_6$)alkyl, SO$_2$(C$_1$-C$_6$)alkyl, —O(C$_1$-C$_4$)alkylene-O—(C$_1$-C$_6$)alkyl, (C$_1$-C$_4$)alkylene-C(O)—O (C$_1$-C$_6$)alkyl, —O(C$_1$-C$_6$)alkyl, (C$_2$-C$_6$)alkenyl, (C$_3$-C$_8$)cycloalkyl, (C$_1$-C$_4$)alkylene-(C$_3$-C$_8$)cycloalkyl, (C$_3$-C$_8$)cycloalkylene-(C$_1$-C$_4$)alkyl, —O(C$_2$-C$_6$)alkenyl, —O(C$_3$-C$_8$)cycloalkyl, —O—(C$_1$-C$_4$)alkylene-(C$_3$-C$_8$)cycloalkyl, —O—(C$_3$-C$_8$)cycloalkylene-(C$_1$-C$_4$)alkyl, (C$_2$-C$_6$)alkynyl, —O(C$_2$-C$_6$)alkynyl, or —NR$_{14}$R$_{15}$, where $R_{14}$ and $R_{15}$ are independently of one another H, (C$_1$-C$_6$)alkyl, (C$_2$-C$_6$)alkenyl, (C$_3$-C$_8$)cycloalkyl, (C$_1$-C$_4$)alkylene-(C$_3$-C$_8$)cycloalkyl, (C$_3$-C$_8$)cycloalkylene-(C$_1$-C$_4$)alkyl, (C$_2$-C$_6$)alkynyl, —C(O)—(C$_1$-C$_6$)alkyl, —C(O)—O—(C$_1$-C$_6$) alkyl, —C(O)—NH—(C$_1$-C$_6$)alkyl, —C(O)—(C$_2$-C$_6$)alkenyl, —C(O)—O—(C$_2$-C$_6$)alkenyl, —C(O)—NH—(C$_2$-C$_6$)alkenyl, —C(O)—(C$_3$-C$_8$)cycloalkyl, —C(O)—O—(C$_3$-C$_8$)cycloalkyl, —C(O)—NH—(C$_3$-C$_8$)cycloalkyl, —C(O)—(C$_1$-C$_4$)alkylene-(C$_3$-C$_8$)cycloalkyl, —C(O)—O—(C$_1$-C$_4$)alkylene-(C$_3$-C$_8$)cycloalkyl, —C(O)—NH—(C$_1$-C$_4$)alkylene-(C$_3$-C$_8$)cycloalkyl, —C(O)—(C$_3$-C$_8$)cycloalkylene-(C$_1$-C$_4$)alkyl, —C(O)—O—(C$_3$-C$_8$)cycloalkylene-(C$_1$-C$_4$) alkyl, —C(O)—NH—(C$_3$-C$_8$)cycloalkylene-(C$_1$-C$_4$)alkyl, —C(O)—(C$_2$-C$_6$)alkynyl, —C(O)—O—(C$_2$-C$_6$)alkynyl or —C(O)—NH—(C$_2$-C$_6$) alkynyl, or is substituted by 1, 2 or 3 substituents independently of one another selected from F, Cl, Br, I, CN, OH, NO$_2$, (C$_1$-C$_6$)alkyl, (C$_2$-C$_6$)alkenyl, (C$_2$-C$_6$)alkynyl, (C$_3$-C$_8$)cycloalkyl, (C$_1$-C$_4$)alkylene-(C$_3$-C$_8$)cycloalkyl, (C$_3$-C$_8$)cycloalkylene-(C$_1$-C$_4$)alkyl, —O(C$_1$-C$_6$)alkyl, —O(C$_2$-C$_6$)alkenyl, —O(C$_2$-C$_6$)alkynyl, —O(C$_3$-C$_8$)cycloalkyl, —O—(C$_1$-C$_4$)alkylene-(C$_3$-C$_8$)cycloalkyl, —O—(C$_3$-C$_8$)cycloalkylene-(C$_1$-C$_4$)alkyl, —O—(C$_1$-C$_4$)alkylene-O—(C$_1$-C$_6$)alkyl, or a radical —NR$_{16}$R$_{17}$, where $R_{16}$ and $R_{17}$ are independently of one another H, (C$_1$-C$_6$)alkyl, (C$_2$-C$_6$)alkenyl, (C$_3$-C$_8$)cycloalkyl, (C$_1$-C$_4$)alkylene-(C$_3$-C$_8$)cycloalkyl, (C$_3$-C$_8$)cycloalkylene-(C$_1$-C$_4$)alkyl, (C$_2$-C$_6$)alkynyl, —C(O)—(C$_1$-C$_6$)alkyl, —C(O)—O—(C$_1$-C$_6$) alkyl, —C(O)—NH—(C$_1$-C$_6$)alkyl, —C(O)—(C$_2$-C$_6$)alkenyl, —C(O)—O—(C$_2$-C$_6$)alkenyl, —C(O)—NH—(C$_2$-C$_6$)alkenyl, —C(O)—(C$_3$-C$_8$)cycloalkyl, —C(O)—O—(C$_3$-C$_8$)cycloalkyl, —C(O)—NH—(C$_3$-C$_8$)cycloalkyl, —C(O)—(C$_1$-C$_4$)alkylene-(C$_3$-C$_8$)cycloalkyl, —C(O)—O—(C$_1$-C$_4$)alkylene-(C$_3$-C$_8$)cycloalkyl, —C(O)—NH—(C$_1$-C$_4$)alkylene-(C$_3$-C$_8$)cycloalkyl, —C(O)—(C$_3$-C$_8$)cycloalkylene-(C$_1$-C$_4$)alkyl, —C(O)—O—(C$_3$-C$_8$)cycloalkylene-(C$_1$-C$_4$) alkyl, —C(O)—NH—(C$_3$-C$_8$)cycloalkylene-(C$_1$-

C$_4$)alkyl, —C(O)—(C$_2$-C$_6$)alkynyl, —C(O)—O—(C$_2$-C$_6$)alkynyl or —C(O)—NH—(C$_2$-C$_6$)alkynyl, or R$_{16}$ and R$_{17}$ together with the N atom to which they are bonded form a 5- or 6-membered heterocycloalkyl radical which optionally contains additionally 0, 1 or 2 ring atoms selected from O or N, and N atoms are substituted by H or (C$_1$-C$_6$)alkyl, or R$_{16}$ and R$_{17}$ together with the N atom to which they are bonded form a 5- or 6-membered heteroaryl radical which optionally contains additionally 0, 1 or 2 ring atoms selected from O or N, R$_5$, R$_6$, R$_7$, R$_8$, R$_9$, R$_{10}$ and R$_{11}$ are independently of one another H or (C$_1$-C$_6$)alkyl, and R$_{12}$ and R$_{13}$ are independently of one another H or (C$_1$-C$_4$)alkyl, where optionally independently of one another one or more H atoms in (C$_1$-C$_6$)alkyl, (C$_1$-C$_6$)alkylene, (C$_1$-C$_4$)alkyl, (C$_1$-C$_4$)alkylene, (C$_2$-C$_6$)alkenyl, (C$_3$-C$_8$)cycloalkyl, (C$_3$-C$_8$)cycloalkylene or (C$_2$-C$_6$)alkynyl radicals may be replaced by F atoms, or a pharmacologically acceptable salt thereof.

2. The compound according to claim 1, wherein one of R$_1$, R$_2$ and R$_3$ is —X-Q-Y.

3. The compound according to claim 1, where n is 1.

4. The compound according to claim 1, wherein L is a covalent bond or a (C$_1$-C$_4$)alkylene group.

5. The compound according to claim 1, wherein n is 1 and L is a covalent bond or a (C$_1$-C$_4$)alkylene group.

6. The compound according to claim 1, wherein
R$_4$ is phenyl or (C$_5$-C$_{14}$)heteroaryl, where phenyl or (C$_5$-C$_{14}$)heteroaryl is substituted by 1, 2 or 3 substituents, and where one of these substituents is a group T-Z.

7. The compound according to claim 1, wherein A is —C(O)OR$_{10}$, —C(O)NR$_{10}$R$_{11}$ or —C(O)NR$_{10}$OH.

8. The compound according to claim 1, wherein
R$_1$, R$_2$ and R$_3$ are independently of one another H, F, Cl, Br, CN, OH, (C$_1$-C$_6$)alkyl, (C$_3$-C$_8$)cycloalkyl, —O(C$_1$-C$_6$)alkyl, —O(C$_3$-C$_8$)cycloalkyl, —OC(O)—(C$_1$-C$_6$)alkyl, —OC(O)—(C$_3$-C$_8$)cycloalkyl, —C(O)O—(C$_1$-C$_6$)alkyl, —C(O)O—(C$_3$-C$_8$)cycloalkyl, —C(O)NR$_5$R$_6$, —NR$_5$R$_6$, —NR$_5$C(O)R$_6$ or a group —X-Q-Y, where
X is a covalent bond, O or NR$_7$,
Q is (C$_1$-C$_4$)alkylene,
Y is —OR$_8$, —NR$_8$R$_9$, —C(O)OR$_8$, —S(O)$_2$OR$_8$, —S(O)$_2$NR$_8$R$_9$, or a five- or six-membered saturated heterocycle containing 1 or 2 ring heteroatoms selected from N or O, in which the N atoms are substituted by H or (C$_1$-C$_6$)-alkyl, or Y is a five- or six-membered aromatic heterocycle having 1, 2 or 3 N ring atoms,
where 1 or 2 radicals of R$_1$, R$_2$ or R$_3$ are —X-Q-Y,
A is —C(O)OR$_{10}$, —C(O)NR$_{10}$R$_{11}$ or —C(O)NR$_{10}$OH,
n is 1,
L is a covalent bond or (C$_1$-C$_4$)alkylene,
R$_4$ is phenyl or (C$_5$-C$_{14}$)heteroaryl, where the phenyl or (C$_5$-C$_{14}$)heteroaryl radical is unsubstituted or is substituted by a group T-Z, where
T is a covalent bond, O, NH or N(C$_1$-C$_4$)alkyl,
Z is phenyl, (C$_5$-C$_{14}$)heteroaryl, or (C$_3$-C$_8$)heterocycloalkyl, where phenyl, (C$_5$-C$_{14}$)heteroaryl or (C$_3$-C$_8$)heterocycloalkyl is unsubstituted or is substituted by 1, 2 or 3 substituents independently of one another selected from F, Cl, Br, CN, OH, (C$_1$-C$_6$)alkyl, SO$_2$(C$_1$-C$_6$)alkyl, —O—(C$_1$-C$_4$)alkylene-O—(C$_1$-C$_6$)alkyl, —O—(C$_1$-C$_6$)alkyl, (C$_3$-C$_8$)cycloalkyl, —O(C$_3$-C$_8$)cycloalkyl, (C$_2$-C$_6$)alkynyl, —O(C$_2$-C$_6$)alkynyl, or —NR$_{14}$R$_{15}$, where
R$_{14}$ and R$_{15}$ are independently of one another H, (C$_1$-C$_6$)alkyl, (C$_3$-C$_8$)cycloalkyl, (C$_2$-C$_6$)alkynyl, —C(O)—(C$_1$-C$_6$)alkyl, —C(O)—O—(C$_1$-C$_6$)alkyl, —C(O)—NH—(C$_1$-C$_6$)alkyl, —C(O)—(C$_3$-C$_8$)cycloalkyl, —C(O)—O—(C$_3$-C$_8$)cycloalkyl, —C(O)—NH—(C$_3$-C$_8$)cycloalkyl, —C(O)—(C$_2$-C$_6$)alkynyl, —C(O)—O—(C$_2$-C$_6$)alkynyl, or —C(O)—NH—(C$_2$-C$_6$)alkynyl, or is substituted by 1, 2 or 3 substituents independently of one another selected from F, Cl, Br, CN, OH, (C$_1$-C$_6$)alkyl, (C$_2$-C$_6$)alkynyl, (C$_3$-C$_8$)cycloalkyl, —O(C$_1$-C$_6$)alkyl, —O(C$_2$-C$_6$)alkynyl, —O(C$_3$-C$_8$)cycloalkyl, —O—(C$_1$-C$_4$)alkylene-O—(C$_1$-C$_6$)alkyl, or a radical —NR$_{16}$R$_{17}$, where
R$_{16}$ and R$_{17}$ are independently of one another H, (C$_1$-C$_6$)alkyl, (C$_3$-C$_8$)cycloalkyl, (C$_2$-C$_6$)alkynyl, —C(O)—(C$_1$-C$_6$)alkyl, —C(O)—O—(C$_1$-C$_6$)alkyl, —C(O)—NH—(C$_1$-C$_6$)alkyl, —C(O)—(C$_3$-C$_8$)cycloalkyl, —C(O)—O—(C$_3$-C$_8$)cycloalkyl, —C(O)—NH—(C$_3$-C$_8$)cycloalkyl, —C(O)—(C$_2$-C$_6$)alkynyl, —C(O)—O—(C$_2$-C$_6$)alkynyl, or —C(O)—NH—(C$_2$-C$_6$)alkynyl, or
R$_{16}$ and R$_{17}$ together with the N atom to which they are bonded form a 5- or 6-membered heterocycloalkyl radical which optionally contains additionally 0, 1 or 2 ring atoms selected from O or N, and N atoms are substituted by H or (C$_1$-C$_6$)alkyl, or
R$_{16}$ and R$_{17}$ together with the N atom to which they are bonded form a 5- or 6-membered heteroaryl radical which optionally contains additionally 0, 1 or 2 ring atoms selected from O or N, and R$_5$, R$_6$, R$_7$, R$_8$, R$_9$, R$_{10}$, and R$_{11}$ are independently of one another H or (C$_1$-C$_6$)alkyl.

9. The compound according to claim 1, wherein
R$_1$, R$_2$ and R$_3$ are independently of one another H, F, Cl, Br, CN, OH, (C$_1$-C$_6$)alkyl, cyclopropyl, —O(C$_1$-C$_6$)alkyl, acetyl, propionyl, —C(O)O—(C$_1$-C$_4$)alkyl, —NR$_5$R$_6$ or a group —X-Q-Y, where
X is O,
Q is (C$_1$-C$_4$)alkylene, and
Y is —O—(C$_1$-C$_4$)alkyl, —NR$_8$R$_9$, —COOH, —C(O)O(C$_1$-C$_4$)alkyl, —SO$_3$H, —S(O)$_2$O(C$_1$-C$_4$)alkyl, —SO$_2$NR$_8$R$_9$, or a five- or six-membered saturated heterocycle containing 1 or 2 ring heteroatoms selected from N or O, in which the N atoms are substituted by H or (C$_1$-C$_4$)-alkyl, or Y is a five- or six-membered aromatic heterocycle having 1 or 2 N atoms,
where one or two radicals of R$_1$, R$_2$ or R$_3$ are a group —X-Q-Y,
A is —COOH, —C(O)NH$_2$ or —C(O)NHOH,
n is 1,
L is a covalent bond,
R$_4$ is phenyl or (C$_5$-C$_{10}$)heteroaryl, where the phenyl or (C$_5$-C$_{10}$)heteroaryl radical is unsubstituted or is substituted by a group T-Z, where
T is a covalent bond or O,
Z is phenyl, or (C$_5$-C$_{10}$)heteroaryl, where phenyl or (C$_5$-C$_{14}$)heteroaryl is unsubstituted or is substituted by 1 or 2 substituents independently of one another selected from F, Cl, Br, CN, OH, (C$_1$-C$_6$)alkyl, —O—(C$_1$-C$_4$)alkylene-O—(C$_1$-C$_6$)alkyl, —O—(C$_1$-C$_6$)alkyl, (C$_2$-C$_6$)alkynyl, or —O(C$_2$-C$_6$)alkynyl, or is substituted by 1 or 2 substituents independently of one another selected from F, Cl, Br, CN, OH, (C$_1$-C$_4$)alkyl, (C$_2$-C$_4$)alkynyl, —O(C$_1$-C$_4$)alkyl, —O(C$_2$-C$_4$)alkynyl, —O—(C$_1$-C$_4$)alkylene-O—(C$_1$-C$_4$)alkyl, or a radical —NR$_{16}$R$_{17}$, where
- R$_{16}$ and R$_{17}$ are independently of one another H, (C$_1$-C$_6$)alkyl, —C(O)—(C$_1$-C$_6$)alkyl, —C(O)—O—(C$_1$-C$_6$)alkyl, or —C(O)—NH—(C$_1$-C$_6$)alkyl, or
- R$_{16}$ and R$_{17}$ together with the N atom to which they are bonded form a 5- or 6-membered heterocycloalkyl radical which optionally contains additionally 0, 1 or 2 ring atoms selected from O or N, and N atoms are substituted by H or (C$_1$-C$_6$)alkyl, or
- R$_{16}$ and R$_{17}$ together with the N atom to which they are bonded form a 5- or 6-membered heteroaryl radical which optionally contains additionally 0, 1 or 2 ring atoms selected from O or N, R$_5$ and R$_6$ are independently of one another H or (C$_1$-C$_6$)alkyl, and R$_8$ and R$_9$ are independently of one another H or (C$_1$-C$_4$)alkyl.

10. The compound according to claim 1, wherein
R$_1$, R$_2$ and R$_3$ are independently of one another H, F, Cl, Br, CN, OH, (C$_1$-C$_4$)alkyl, —(C$_1$-C$_6$)alkyl, or a group —X-Q-Y, where
X is O,
Q is (C$_1$-C$_4$)alkylene, and
Y is —O—(C$_1$-C$_4$)alkyl, —NR$_8$R$_9$, —COOH, —C(O)O(C$_1$-C$_4$)alkyl, —SO$_3$H, —S(O)$_2$O(C$_1$-C$_4$)alkyl, or a heterocycle selected from piperidinyl, morpholinyl, pyrrolidinyl, imidazolyl, pyrazolyl, piperazinyl or N-methyl-piperazinyl,
where one or two radicals of R$_1$, R$_2$ or R$_3$ are a group —X-Q-Y,
A is —COOH, —C(O)NH$_2$ or —C(O)NHOH,
n is 1,
L is a covalent bond,
R$_4$ is phenyl, where the phenyl radical is unsubstituted or is substituted by a group T-Z, where
T is a covalent bond or O,
Z is phenyl, where phenyl is unsubstituted or is substituted by 1 or 2 substituents independently of one another selected from F, Cl, Br, CN, OH, (C$_1$-C$_6$)alkyl, —O—(C$_1$-C$_4$)alkylene-O—(C$_1$-C$_6$)alkyl, —O—(C$_1$-C$_6$)alkyl, (C$_2$-C$_6$)alkynyl, or —O(C$_2$-C$_6$)alkynyl,
or is substituted by 1 or 2 substituents independently of one another selected from F, Cl, Br, CN, OH, (C$_1$-C$_4$)alkyl, (C$_2$-C$_4$)alkynyl, —O(C$_1$-C$_4$)alkyl, —O(C$_2$-C$_4$)alkynyl, —O—(C$_1$-C$_4$)alkylene-O—(C$_1$-C$_4$)alkyl, or a radical —NR$_{16}$R$_{17}$, where
- R$_{16}$ and R$_{17}$ are independently of one another H, (C$_1$-C$_6$)alkyl, —C(O)—(C$_1$-C$_6$)alkyl, —C(O)—O—(C$_1$-C$_6$)alkyl, or —C(O)—NH—(C$_1$-C$_6$)alkyl, or
- R$_{16}$ and R$_{17}$ together with the N atom to which they are bonded form a 5- or 6-membered heterocycloalkyl radical which optionally contains additionally 0, 1 or 2 ring atoms selected from O or N, and N atoms are substituted by H or (C$_1$-C$_6$)alkyl, or
- R$_{16}$ and R$_{17}$ together with the N atom to which they are bonded form a 5- or 6-membered heteroaryl radical which optionally contains additionally 0, 1 or 2 ring atoms selected from O or N, and R$_8$ and R$_9$ are independently of one another H or (C$_1$-C$_4$)alkyl.

11. The compound according to claim 1, wherein
R$_1$, R$_2$ and R$_3$ are independently of one another H, F, Cl, Br, CN, (C$_1$-C$_4$)alkyl or a group —X-Q-Y, where
X is O,
Q is (C$_2$-C$_3$)alkylene, and
Y is —O—(C$_1$-C$_4$)alkyl, —NR$_8$R$_9$, or a heterocycle selected from piperidinyl, morpholinyl, pyrrolidinyl, imidazolyl, pyrazolyl, piperazinyl or N-methylpiperazinyl,
where a radical of R$_1$, R$_2$ or R$_3$ is a group —X-Q-Y,
A is —COOH or —C(O)NHOH,
n is 1,
L is a covalent bond,
R$_4$ is phenyl, where the phenyl radical is unsubstituted or is substituted by a group T-Z, where
T is O, and
Z is a phenyl group, which is unsubstituted or is substituted by 1 or 2 substituents independently of one another selected from H, F, Cl, CN, OH, (C$_1$-C$_4$)alkyl, or —O(C$_1$-C$_6$)alkyl,
or where phenyl is substituted by 1 or 2 (C$_1$-C$_4$)alkyl radicals, and R$_8$ and R$_9$ are independently of one another H or (C$_1$-C$_4$)alkyl.

12. The compound according to claim 1, wherein
R$_1$, R$_2$ and R$_3$ are independently of one another H, F, Cl, Br, CN, (C$_1$-C$_4$)alkyl or a group —X-Q-Y, where
X is O,
Q is (C$_2$-C$_3$)alkylene, and
Y is —O—(C$_1$-C$_4$)alkyl, —NR$_8$R$_9$, or a heterocycle selected from piperidinyl, morpholinyl, pyrrolidinyl, imidazolyl, pyrazolyl, piperazinyl or N-methylpiperazinyl,
where a radical of R$_1$, R$_2$ or R$_3$ is a group —X-Q-Y,
A is —COOH or —C(O)NHOH,
n is 1,
L is a covalent bond,
R$_4$ is phenyl, where the phenyl radical is unsubstituted or is substituted by a group T-Z, where
T is O, and
Z is a phenyl group, which is unsubstituted or is substituted by 1 or 2 substituents independently of one another selected from F or —O(C$_1$-C$_6$)alkyl,
or where phenyl is substituted by 1 or 2 (C$_1$-C$_4$)alkyl radicals, and R$_8$ and R$_9$ are independently of one another H or (C$_1$-C$_4$)alkyl.

13. A process for preparing the compound of formula (I) according to claim 1, wherein R$_1$-R$_9$, R$_{12}$-R$_{17}$, n, L, X, Q, Y, T and Z have the meaning as defined in claim 1, comprising reacting a tetrahydroisoquinoline of formula (XXII)

(XXII)

with a sulfonyl chloride (III)

(III)

to form a sulfonamide (XXIII)

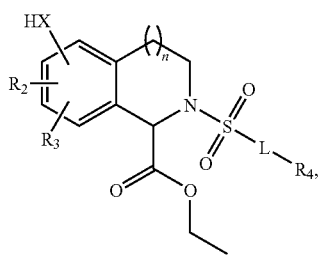
(XXIII)

reacting the sulfonamide (XXIII) with a dialkyl azodicarboxylate, triphenylphosphine and a compound HO-Q-Y (V) to give a compound (XXIV)

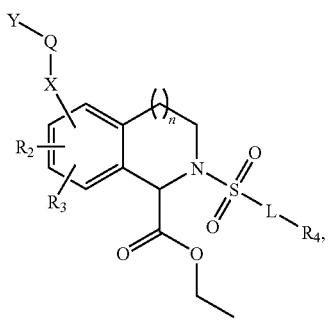
(XXIV)

hydrolyzing the compound (XXIV) using a base, to form a compound of formula (I) wherein A is —C(O)OR$_{10}$, and R$_{10}$ is H, and optionally reacting the compound of formula (I) wherein A is —C(O)OR$_{10}$, and R$_{10}$ is H with a (C$_1$-C$_6$)alkyl chloride, to form a compound of formula (I) wherein A is —C(O)OR$_{10}$, and R$_{10}$ is (C$_1$-C$_6$)alkyl, or optionally reacting the compound of formula (I) wherein A is —C(O)OR$_{10}$, and R$_{10}$ is H with Cl—COOEt and subsequent addition of R$_{10}$HNOTMS, to form a compound of formula (I) wherein A is —C(O)NR$_{10}$OH, or optionally reducing the compound of formula (I) wherein A is —C(O)OR$_{10}$, and R$_{10}$ is H with a hydride to give an alcohol, converting the alcohol group into a leaving group and then reacting with a compound containing an SH— group to form a compound of formula (I) wherein A is —CH$_2$SH, or optionally reacting the compound of formula (I) wherein A is —C(O)OR$_{10}$, and R$_{10}$ is H with an amine (C$_1$-C$_6$) alkyl-NH$_2$ in the presence of a base to form a compound of formula (I) wherein A is —C(O)NR$_{10}$R$_{11}$.

14. The process according to claim 13, where n is 1.

15. A pharmaceutical composition comprising a pharmaceutically effective amount of the compound according to claim 1 or a pharmaceutically acceptable salt thereof, and a pharmaceutically suitable and physiologically tolerated carrier, additive excipient.

* * * * *